United States Patent
Atkinson et al.

(10) Patent No.: US 10,849,897 B2
(45) Date of Patent: Dec. 1, 2020

(54) PYRIDYL DERIVATIVES AS BROMODOMAIN INHIBITORS

(71) Applicant: GLAXOSMITHKLINE INTELLECTUAL PROPERTY (NO.2) LIMITED, Brentford (GB)

(72) Inventors: Stephen John Atkinson, Stevenage (GB); Emmanuel Hubert Demont, Steveange (GB); Lee Andrew Harrison, Stevenage (GB); Etienne Levernier, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GLAXOSMITHKLINE INTELLECTUAL PROPERTY (NO.2) LIMITED, Brentford (GB)

( * ) Notice: Subject to any disclaimer, the term of this patent is extended or adjusted under 35 U.S.C. 154(b) by 0 days.

(21) Appl. No.: 16/489,876

(22) PCT Filed: Feb. 27, 2018

(86) PCT No.: PCT/EP2018/054730
§ 371 (c)(1),
(2) Date: Aug. 29, 2019

(87) PCT Pub. No.: WO2018/158210
PCT Pub. Date: Sep. 7, 2018

(65) Prior Publication Data
US 2020/0009140 A1    Jan. 9, 2020

(30) Foreign Application Priority Data
Mar. 1, 2017   (GB) .................................. 1703282.2

(51) Int. Cl.
| | | |
|---|---|---|
| *A61K 31/506* | (2006.01) | |
| *A61K 31/44* | (2006.01) | |
| *A61K 31/4439* | (2006.01) | |
| *A61K 31/444* | (2006.01) | |
| *A61K 31/501* | (2006.01) | |
| *C07D 213/81* | (2006.01) | |
| *C07D 401/12* | (2006.01) | |
| *C07D 401/14* | (2006.01) | |
| *C07D 413/12* | (2006.01) | |
| *C07D 417/12* | (2006.01) | |

(52) U.S. Cl.
CPC .......... *A61K 31/506* (2013.01); *A61K 31/44* (2013.01); *A61K 31/444* (2013.01); *A61K 31/4439* (2013.01); *A61K 31/501* (2013.01); *C07D 213/81* (2013.01); *C07D 401/12* (2013.01); *C07D 401/14* (2013.01); *C07D 413/12* (2013.01); *C07D 417/12* (2013.01)

(58) Field of Classification Search
CPC .. A61K 31/506; A61K 31/44; A61K 31/4439; A61K 31/444; A61K 31/501; C07D 213/81; C07D 401/12; C07D 401/14; C07D 413/12; C07D 417/12; C07D 401/06; A61P 37/00
See application file for complete search history.

(56) References Cited

U.S. PATENT DOCUMENTS

| | | |
|---|---|---|
| 2012/0208814 A1 | 8/2012 | Demont et al. |
| 2014/0179648 A1 | 6/2014 | Liu et al. |

FOREIGN PATENT DOCUMENTS

| | | | |
|---|---|---|---|
| EP | 1 357 111 A1 | 10/2003 | |
| EP | 1 433 788 A1 | 6/2004 | |
| EP | 1 477 186 A1 | 11/2004 | |
| WO | WO 2004/033446 A1 | 4/2004 | |
| WO | WO 2014/074675 A1 | 5/2014 | |
| WO | WO 2014/096965 A2 | 6/2014 | |
| WO | WO 2015/015318 A2 | 2/2015 | |
| WO | WO 2017/037116 A1 | 3/2017 | |
| WO | WO 2017/060180 A1 | 4/2017 | |
| WO | WO 2017/174621 A1 | 10/2017 | |
| WO | WO 2017/202742 A1 | 11/2017 | |

OTHER PUBLICATIONS

Alqahtani, A., "Bronnodonnain and extra-terminal motif inhibitors: a review of preclinical and clinical advances in cancer therapy." Future science OA 5.3 (2019): FSO372.*
Legal Definition of Medical Treatment; Law Insider (https://www.lawinsider.com/dictionary/medical-treatment 2020; p. 1-9.*
Dittmer et al., "Models for the Pyridine Nucleotide Coenzymes. Synthesis and Properties of Bridged Dinicotinamide Derivatives[1-3]", *J. Org. Chem.*, vol. 38, No. 16, pp. 2873-2882 (1973).
Gallenkamp et al., "Bromodomains and Their Pharmacological Inhibitors", *ChemMedChem*, vol. 9, No. 3, pp. 438-464 (2014).
Garnier et al., "BET bromodomain inhibitors: a patent review", *Expert Opinion on Therapeutic Patents*, vol. 24, No. 2, pp. 185-199 (2014).
International Search Report for International application No. PCT/EP2016/070519, dated Oct. 20, 2016, 4 pages.
International Search Report for International application No. PCT/EP2016/072216, dated Sep. 20, 2016, 3 pages.
International Search Report for International application No. PCT/EP2016/073532, dated Nov. 30, 2016, 5 pages.

(Continued)

*Primary Examiner* — John M Mauro
(74) *Attorney, Agent, or Firm* — Robert H. Brink; Duke M. Fitch; Edward R. Gimmi

(57) ABSTRACT

The present invention is directed to pyridyl derivatives which are bromodomain inhibitors, pharmaceutical compositions comprising the compounds and the use of the compounds or the compositions in the treatment of various diseases or conditions.

20 Claims, No Drawings

(56) References Cited

OTHER PUBLICATIONS

International Search Report for International application No. PCT/EP2017/058050, dated May 24, 2017, 5 pages.
International Search Report for International application No. PCT/EP2017/062208, dated Jul. 6, 2017, 5 pages.
International Search Report for International application No. PCT/EP2018/054730, dated May 4, 2018, 5 pages.
International Search Report for International application No. PCT/EP2018/054733, dated Jun. 11, 2018, 5 pages.
Non-Final Office Action for U.S. Appl. No. 15/766,222, USPTO, notification dated Oct. 4, 2018, 9 pages.
Notice of Allowance for U.S. Appl. No. 15/762,229, USPTO, dated Dec. 11, 2018, 9 pages.
Notice of Allowance for U.S. Appl. No. 15/766,222, USPTO, dated Jan. 17, 2019, 6 pages.
Notice of Allowance for U.S. Appl. No. 15/762,229, USPTO, dated Mar. 20, 2019, 9 pages.
Restriction Requirement for U.S. Appl. No. 15/757,199, USPTO, notification dated Feb. 11, 2019, 9 pages \* cited by examiner

PYRIDYL DERIVATIVES AS BROMODOMAIN INHIBITORS

This application is a § 371 of International Application No. PCT/EP2018/054730, filed 27 Feb. 2018, which claims the priority of GB 1703282.2, filed 1 Mar. 2017.

FIELD OF THE INVENTION

The present invention is directed to pyridyl derivatives which are bromodomain inhibitors, pharmaceutical compositions comprising the compounds and the use of the compounds or the compositions in the treatment of various diseases or conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation and SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al., *J Med. Chem.*, 2011, 54, 3827-3838).

Chan et al. report that BET bromodomain inhibition suppresses transcriptional responses to cytokine-Jak-STAT signalling in a gene-specific maner in human monocytes, which suggests that BET inhibition reduces inflammation partially through suppression of cytokine activity. (Chan et al., *Eur. J. Immunol.*, 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.*, 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. *Nature Communications*, 2014, 5, 5418).

PCT patent applications PCT/EP2016/070519, PCT/EP2016/072216 and PCT/EP2016/073532 each describe a series of pyridone derivatives as bromodomain inhibitors.

SUMMARY OF THE INVENTION

The invention is directed to compounds of formula (I)

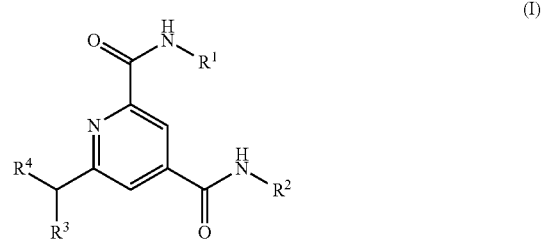

or a salt thereof
wherein:
$R^1$ is —$C_{1-3}$alkyl or cyclopropyl;
$R^2$ is H, —$CH_3$, $C_{2-6}$alkyl optionally substituted by one, two, three, four or five fluoro, —$C_{2-6}$alkylOR$^7$, —$C_{2-6}$alkylNR$^7$R$^8$, —$(CH_2)_m$SO$_2$C$_{1-3}$alkyl, —$(CH_2)_m$C(O)NR$^7$R$^8$, —$(CH_2)_m$CN, —$(CH_2)_m$CO$_2$R$^7$, —$(CH_2)_m$NHCO$_2$C(CH$_3$)$_3$; or
$R^2$ is —$(CH_2)_n$C$_{5-6}$heteroaryl wherein C$_{5-6}$heteroaryl is optionally substituted by one or two substituents independently selected from halo, —$C_{1-4}$alkyl, —$C_{3-4}$cycloalkyl and —$C_{0-4}$alkylOR$^5$;
$R^3$ is H, —$C_{1-4}$alkyl, cyclopropyl, fluoro, chloro, —CH$_2$F, —$C_{0-3}$alkylOR$^5$ or —$C_{0-3}$alkylCN;
$R^4$ is phenyl or a heteroaryl group wherein each are optionally substituted by one, two or three R$^6$ groups which may be the same or different;
$R^5$ is H or —$C_{1-3}$alkyl;
each $R^6$ is independently halo, —$C_{1-4}$alkyl, —$C_{0-3}$alkylOR$^7$, —$C_{0-3}$alkylNR$^9$R$^{10}$, —$C_{0-3}$alkyl-CONR$^9$R$^{10}$, —CN, oxo, —SO$_2$—$C_{1-3}$alkyl or —SO$_2$NR$^9$R$^{10}$;
$R^7$ and $R^8$ are each independently selected from —H, —$C_{1-3}$alkyl and —$C_{2-4}$alkylOC$_{0-3}$alkyl;
$R^9$ and $R^{10}$ are each independently selected from —H and —$C_{1-3}$alkyl; or $R^9$ and $R^{10}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;
m is an integer selected from 2, 3 or 4; and
n is an integer selected from 0, 1, 2, 3 or 4.

Compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis and cancer. Accordingly, the invention is further directed to pharmaceutical compositions comprising a compound of formula (I), or a pharmaceutically acceptable salt thereof. The invention is still further directed to methods of treatment of diseases or conditions associated with bromodomains using a compound of formula (I) or a pharmaceutically acceptable salt thereof, or a pharmaceutical composition comprising a compound of formula (I) or a pharmaceutically acceptable salt thereof.

DETAILED DESCRIPTION OF THE INVENTION

Compounds of formula (I) and salts thereof are referred to herein as "compounds of the invention".

"BD2" refers to Binding Domain 2 of any of the the BET family of proteins BRD2, BRD3, BRD4 or BRDT.

"Alkyl" refers to a saturated hydrocarbon chain having the specified number of carbon atoms. For example, the term "$C_{1-3}$alkyl" or "$C_{1-4}$alkyl" as used herein refers to a straight or branched alkyl group having from 1 to 3 carbon atoms or 1 to 4 carbon atoms respectively. Further, the term "$C_{0-3}$alkyl" refers to a straight or branched alkyl group having from 0 (i.e. a bond) to 3 carbon atoms. Representative branched alkyl groups have one, two or three branches. An alkyl group may form part of a chain, for example, —$C_{0-3}$alkyl$OR^5$ refers to a straight or branched alkyl chain having from 0 (i.e. a bond) to 3 carbon atoms linked to a group $R^5$. "Alkyl" includes, but is not limited to, methyl, ethyl, n-propyl, iso-propyl, n-butyl, iso-butyl, t-butyl, pentyl and hexyl.

"Halo" refers to a halogen radical, for example, fluoro, chloro, bromo, or iodo.

"Heteroaryl" refers to a monocyclic or bicyclic group having 5, 6, 8, 9, 10 or 11 member atoms, including 1, 2 or 3 heteroatoms independently selected from nitrogen, sulphur and oxygen, wherein at least a portion of the group is aromatic. The point of attachment to the rest of the molecule may be by any suitable carbon or nitrogen atom. Examples of "heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, benzazepinyl, 2,3,4,5-tetrahydro-1H-benzo[d]azepinyl, indolizinyl, indolyl, indolinyl, isoindolyl, dihydroindolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, imidazopyridinyl, pyrazolopyridinyl, pyrrolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

"$C_{5-6}$heteroaryl" refers to a monocyclic aromatic group having 5 or 6 member atoms, including 1, 2, 3 or 4 heteroatoms independently selected from nitrogen, sulphur and oxygen. The point of attachment to the rest of the molecule may be by any suitable carbon or nitrogen atom. Examples of "$C_{5-6}$heteroaryl" groups include, but are not limited to, furanyl, thienyl, pyrrolyl, triazolyl, thiazolyl, oxazolyl, isoxazolyl, oxadiazolyl, imidazolyl, pyrazolyl, triazolyl, tetrazolyl, isoxazolyl, pyridinyl, pyridazinyl, pyrazinyl and pyrimidinyl.

"Heteroatom" refers to a nitrogen, sulfur, or oxygen atom.

"4 to 7-membered heterocyclyl" refers to a non-aromatic heterocyclic ring system containing 4, 5, 6 or 7 ring member atoms, including one heteroatom and optionally containing a further heteroatom selected from nitrogen, oxygen or sulphur. Examples of "4 to 7-membered heterocyclyl" groups include, but are not limited to, azetidinyl, pyrrolidinyl, piperidinyl, piperazinyl and morpholinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group attached to a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient are avoided. In addition, each excipient must of course be pharmaceutically acceptable e.g. of sufficiently high purity.

"rac" refers to the racemic mixture of the compounds of formula (I).

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic mixtures, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where diastereoisomers are represented and only the relative stereochemistry is referred to, the bold or hashed solid bond symbols (━/⁞⁞⁞⁞⁞) are used. Where the absolute stereochemistry is known and the compound is a single enantiomer, the bold or hashed wedges symbols (◤/⁞⁞⁞⁞⁞) are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that included within the scope of the invention are solvates, isomers and polymorphic forms of the compounds of formula (I) and salts thereof.

STATEMENT OF THE INVENTION

In a first aspect there are provided compounds of formula (I):

(I)

or a salt thereof $R^1$ is —$C_{1-3}$alkyl or cyclopropyl;

$R^2$ is —H, —$CH_3$, $C_{2-6}$alkyl optionally substituted by up to five fluoro, —$C_{2-6}$alkylOR$^7$, —$C_{2-6}$alkylINR$^7$R$^8$, —$(CH_2)_mSO_2C_{1-3}$alkyl, —$(CH_2)_mC(O)NR^7R^8$, —$(CH_2)_mCN$, —$(CH_2)_mCO_2R^7$, —$(CH_2)_mNHCO_2C(CH_3)_3$; or $R^2$ is —$(CH_2)_nC_{5-6}$heteroaryl wherein $C_{5-6}$heteroaryl is optionally substituted by one or two substituents independently selected from halo, —$C_{1-4}$alkyl, —$C_{3-4}$cycloalkyl and —$C_{0-4}$alkylOR$^5$;

$R^3$ is —H, —$C_{1-4}$alkyl, cyclopropyl, fluoro, chloro, —$CH_2F$, $C_{0-3}$alkylOR$^5$ or —$C_{0-3}$alkylCN;

$R^4$ is phenyl or a heteroaryl group wherein each are optionally substituted by one, two or three $R^6$ groups which may be the same or different;

$R^5$ is —H or —$C_{1-3}$alkyl;

each $R^6$ is independently halo, —$C_{1-4}$alkyl, —$C_{0-3}$alkylOR$^7$, —$C_{0-3}$alkylNR$^9$R$^{10}$, —$C_{0-3}$alkyl-CONR$^9$R$^{10}$, —CN, oxo, —$SO_2$—$C_{1-3}$alkyl or —$SO_2NR^9R^{10}$;

$R^7$ and $R^8$ are each independently selected from —H, —$C_{1-3}$alkyl and —$C_{2-4}$alkylOC$_{0-3}$alkyl;

$R^9$ and $R^{10}$ are each independently selected from —H and —$C_{1-3}$alkyl; or $R^9$ and $R^{10}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH and F;

m is an integer selected from 2, 3 or 4; and n is an integer selected from 0, 1, 2, 3 or 4.

In one embodiment $R^1$ is methyl.

In one embodiment $R^2$ is H.

In one embodiment $R^2$ is selected from methyl, ethyl, propyl, iso-propyl, butyl, —$CH_2CH_2CH(CH_3)_2$, —$CH_2CH(CH_3)_2$, —$CH_2CH_2OR^7$, —$CH_2CH_2CH_2OR^7$, —$CH_2CH(CH_3)OR^7$, —$CH_2CH_2CH(CH_3)OR^7$, —$CH_2CH_2CH(OR^7)_2$, —$CH_2CH_2CH(CH_3)NR^7R^8$, —$CH_2CH_2CH_2NR^7R^8$, —$(CH_2)_mSO_2CH_3$, —$(CH_2)_mC(O)NHCH_3$, —$(CH_2)_mCN$, —$(CH_2)_mCO_2R^7$, —$(CH_2)_mCF_3$ and —$(CH_2)_mNHCO_2C(CH_3)_3$.

In another embodiment $R^2$ is —$C_{1-6}$alkyl selected from methyl, ethyl, propyl, iso-propyl, butyl, —$CH_2CH_2CH(CH_3)_2$ and —$CH_2CH(CH_3)_2$. In another embodiment $R^2$ is —$C_{1-6}$alkylOR$^7$ selected from —$CH_2CH_2OR^7$, —$CH_2CH_2CH_2OR^7$, —$CH_2CH(CH_3)OR^7$, —$CH_2CH_2CH$(CH$_3$)OR$^7$ and —$CH_2CH_2CH(OR^7)_2$. In another embodiment $R^2$ is —$C_{1-6}$alkylNR$^7R^8$ selected from —$CH_2CH_2CH$(CH$_3$)NR$^7R^8$ and —$CH_2CH_2CH_2NR^7R^8$. In another embodiment $R^2$ is —$(CH_2)_mSO_2CH_3$. In another embodiment $R^2$ is —$(CH_2)_mC(O)NHCH_3$. In another embodiment $R^2$ is —$(CH_2)_mCN$. In another embodiment $R^2$ is —$(CH_2)_mCO_2R^7$. In another embodiment $R^2$ is —$(CH_2)_mCF_3$. In another embodiment $R^2$ is —$(CH_2)_mNHCO_2C(CH_3)_3$.

In another embodiment $R^2$ is —$(CH_2)_nC_{5-6}$heteroaryl wherein the $C_{5-6}$heteroaryl is selected from furanyl, thienyl, pyrrolyl, triazolyl, thiazolyl, oxazolyl, isoxazolyl, oxadiazolyl, imidazolyl, pyrazolyl, triazolyl, tetrazolyl, isoxazolyl, pyridinyl, pyridazinyl, pyrazinyl and pyrimidinyl said groups being optionally substituted by one or two substituents independently selected from halo, $C_{1-4}$alkyl (such as methyl), $C_{3-4}$cycloalkyl and —$C_{0-3}$alkylOR$^5$.

In another embodiment there is provided compounds of formula (I) in which $R^2$ is —$(CH_2)_nC_{5-6}$heteroaryl wherein the $C_{5-6}$heteroaryl is pyrazolyl optionally substituted by $C_{1-4}$alkyl or —$C_{0-3}$alkylOR$^5$. In a particular embodiment there is provided compounds of formula (I) in which $R^2$ is —$(CH_2)_nC_{5-6}$heteroaryl wherein the $C_{5-6}$heteroaryl is selected from the group consisting of wherein * denotes the point of attachment to the alkyl residue.

In one embodiment $R^3$ is —H, methyl, fluoro, —$OCH_3$ or —OH.

In one embodiment $R^4$ is phenyl optionally substituted by one, two or three $R^6$ groups which may be the same or different. In another embodiment $R^4$ is unsubstituted phenyl.

In another embodiment $R^4$ is a heteroaryl group which is indolyl (e.g. 1H-indol-4-yl) optionally substituted by one, two or three $R^6$ groups which may be the same or different. In another embodiment $R^4$ is a heteroaryl group which is 1H-indol-4-yl.

In one embodiment each $R^6$ is independently halo, —$C_{1-4}$alkyl or —$C_{0-3}$alkylOR$^7$.

In one embodiment m is 2 or 3.

In one embodiment n is 0, 1 or 2. In one embodiment n is 0 or 2. In a further embodiment n is 0. In a yet further embodiment n is 2.

It is to be understood that the present invention covers all combinations of substituent groups described hereinabove.

Compounds of the invention include the compounds of Examples 1 to 81 and salts thereof.

In one embodiment the compound of formula (I) is selected from:

6-Benzyl-N²-methyl-N⁴-(1-methyl-1H-pyrazol-4-yl)pyridine-2,4-dicarboxamide;
6-Benzyl-N²-methyl-N⁴-(1H-pyrazol-4-yl)pyridine-2,4-dicarboxamide;
(S)-N²-Methyl-6-(1-phenylethyl)-N⁴-(1pyrazol-4-yl)pyridine-2,4-dicarboxamide; and
(S)-6-(Methoxy(phenyl)methyl)-N²-methyl-N⁴-(1H-pyrazol-4-yl)pyridine-2,4-dicarboxamide
or a salt thereof.

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject (e.g. a human subject) in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, acute alcoholic hepatitis, chronic alcoholic hepatitis, alcoholic steato-hepatitis, non-alcoholic steato-hepatitis (NASH), cirrhosis, Childs-Pugh cirrhosis, autoimmune hepatitis, fulminant hepatitis, chronic viral hepatitis, alcoholic liver disease, systemic sclerosis, systemic sclerosis with associated interstitial lung disease, sarcoidosis, neurosarcoidosis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement, acute rejection of transplanted organs and systemic sclerosis.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), pulmonary arterial hypertension, cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, pulmonary fibrosis, cystic fibrosis, progressive massive fibrosis, renal fibrosis, liver fibrosis, liver cirrhosis, non-alcoholic steatohepatitis (NASH), non-alcoholic fatty liver disease (NAFLD), post-operative stricture, keloid scar formation, scleroderma (including morphea and systemic sclerosis), cardiac fibrosis, atrial fibrosis, endomyocardial fibrosis, old myocardial infarction, arthrofibrosis, Dupuytren's contracture, mediastinal, myelofibrosis, Peyronie's disease, nephrogenic systemic fibrosis, retroperitoneal fibrosis and adhesive capsulitis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer. In another embodiment the cancer is prostate cancer. In another embodiment the cancer is castration resistant prostate cancer.

Bromodomain inhibitors may be useful in the treatment of diseases associated with systemic inflammatory response syndrome, such as sepsis, burns, pancreatitis, major trauma, haemorrhage and ischaemia. In this embodiment, the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain containing protein which comprises contacting the bromodomain containing protein with a compound of formula (I) or a pharmaceutically acceptable salt thereof.

As used herein the reference to the "treatment" of a particular disease or condition includes the prevention or prophylaxis of such a disease or condition.

Pharmaceutical Compositions/Routes of Administration/Dosages

Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. A pharmaceutical composition comprising a compound of formula (I) or a pharmaceutically acceptable salt thereof may be prepared by, for example, admixture at ambient temperature and atmospheric pressure. The pharmaceutical composition can be used in the treatment of any of the conditions described herein.

In a further aspect the invention is directed to pharmaceutical compositions for the treatment of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subject compliance.

Suitable pharmaceutically-acceptable excipients include the following types of excipients: carriers, diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral administration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfte anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in International Patent Application Publication No. WO 2005/044354 A1.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other theraputically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I)

and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents (such as PD-1 inhibitors, including nivolumab and pembrolizumab, and CTLA-4 inhibitors, including ipilimumab); proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

It will be clear to a person skilled in the art that, where appropriate, the other therapeutic agent(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic agent. It will be clear also that, where appropriate, the therapeutic agents may be used in optically pure form.

The combinations referred to above may conveniently be presented for use in the form of a pharmaceutical composition and thus pharmaceutical compositions comprising a combination as defined above together with a pharmaceutically acceptable excipient represent a further aspect of the invention.

General Synthetic Routes

The compounds of the invention may be made by a variety of methods. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in any of the Schemes below:

Scheme 1:

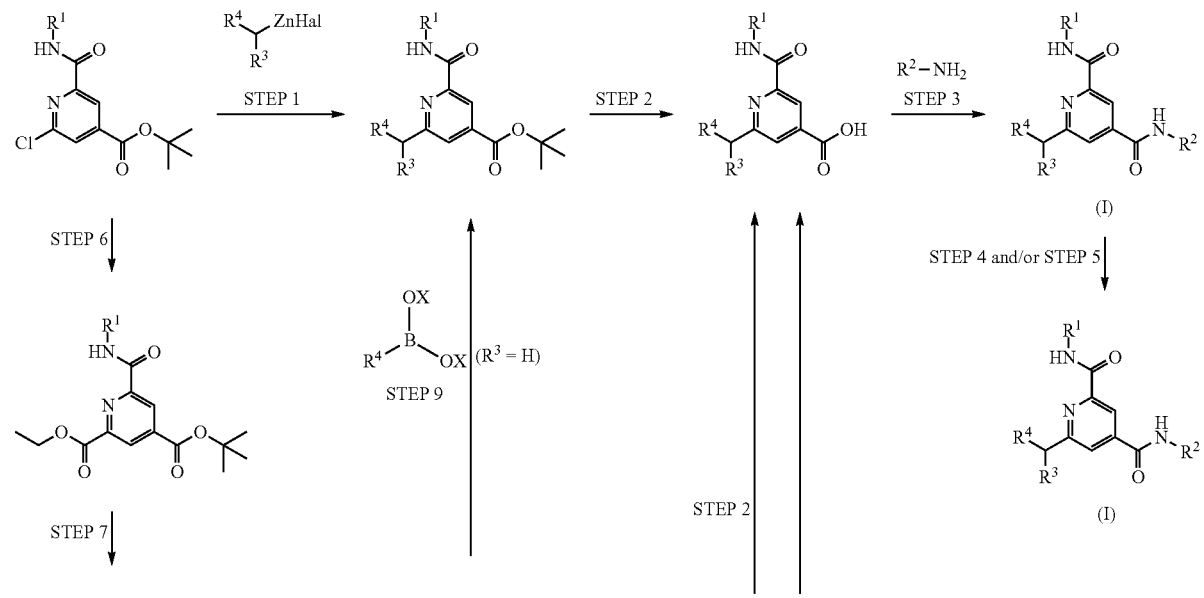

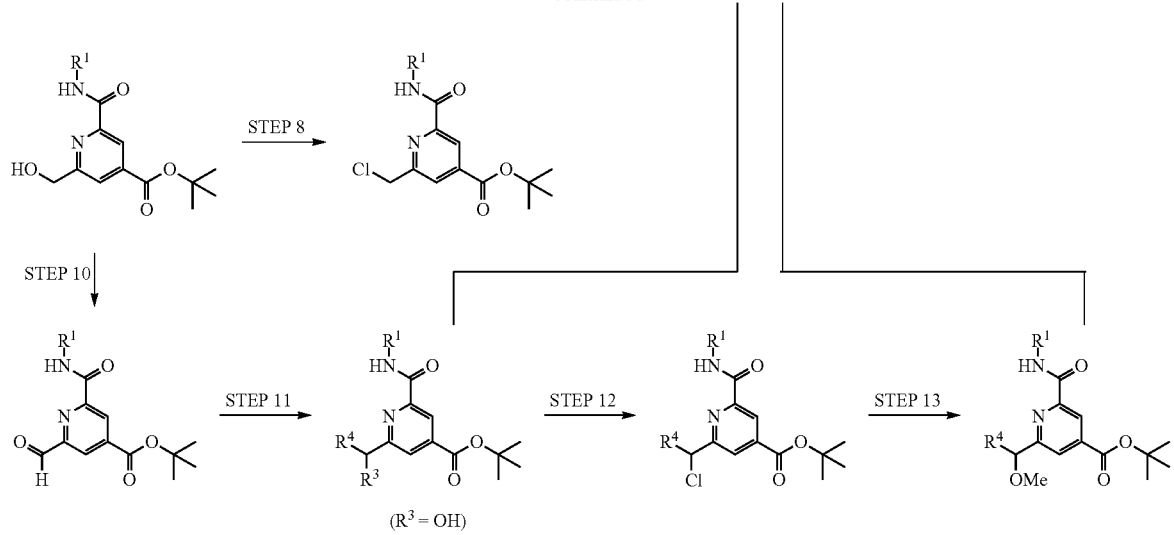

-continued (R³ = OH)

wherein R¹, R², R³ and R⁴ are as described above, Hal is chlorine or bromine and X is either H or joined together to form a cyclic boronate ester, such as —C(Me)₂C(Me)₂-.

In respect of the steps shown in Scheme 1 above the following reaction conditions may be utilised:

Step 1: is a Negishi cross coupling and may be carried out using a benzylzinc halide of formula R⁴CH(R³)ZnHal, in the presence of a palladium catalyst, such as PdCl₂(PPh₃)₂, optionally in the presence of an alternative phosphine ligand, in a suitable solvent, such as THF, at a suitable temperature, such as 70° C.

Step 2: is an acid-mediated ester cleavage and may be carried out using any suitable acid, such as TFA, optionally in a suitable solvent, such as DCM, at a suitable temperature, such as room temperature.

Step 3: is an amide coupling reaction and may be carried out using an amine reagent, R²—NH₂, in the presence of a suitable tertiary amine, such as triethylamine or DIPEA, in the presence of a suitable amide coupling reactant, such as HATU, in a suitable solvent, such as DCM or DMF, at a suitable temperature, such as room temperature.

Step 4: is an optional deprotection step to remove a protecting group, such as BOC and may be carried out using an acid such as TFA or HCl, in the presence of a suitable solvent, such as DCM or 1,4-dioxane, at a suitable temperature, such as room temperature.

Step 5: is an optional chiral separation, using a suitable chiral HPLC column and a suitable solvent system.

Step 6: is a carbonylation reaction and may be carried out using an alcohol reagent, such as EtOH, in the presence of a tertiary amine, such as triethylamine, in the presence of a palladium catalyst, such as [(R)-(+)-2,2'-bis(diphenylphosphino)-1,1'-binaphthyl]palladium(II) chloride, optionally in the presence of an alternative phosphine ligand, in the presence of carbon monoxide, in a suitable solvent, such as DMF, at a suitable temperature, such as 70° C.

Step 7: is a reduction and may be carried out using a reducing agent or combination of reagents, such as sodium borohydride and calcium chloride, in a suitable solvent or solvent mixture, such as ethanol and 2-MeTHF, at a suitable temperature, such as 0° C. to room temperature.

Step 8: is a chlorination reaction and may be carried out using a chlorinating reagent, such as thionyl chloride, in the presence of a suitable solvent, such as DCM, at a suitable temperature, such as room temperature.

Step 9: is a cross-coupling reaction, such as a Suzuki coupling and may be carried out using an arylmetal species, such as a arylboronic acid or arylboronate ester, R⁴—B(OX)₂ in the presence of a suitable palladium catalyst, such as PdCl₂(PPh₃)₂, optionally in the presence of an alternative phosphine ligand, in the presence of a suitable base, such as potassium carbonate, in the presence of a suitable solvent or solvent mixture, such as 1,4-dioxane and water, at a suitable temperature, such as 120° C.

Step 10: is an oxidation and may be carried out using a suitable oxidant, such as Dess-Martin periodinane in a suitable solvent, such as DCM, at a suitable temperature, such as room temperature.

Step 11: is a Grignard addition to an aldehyde, using a suitable Grignard reagent, such as phenylmagnesium bromide, in a suitable solvent, such as THF, at a suitable temperature, such as 0° C.

Step 12: is a substitution reaction of an alcohol with a halide, such as chloride, using a suitable chlorinating reagent, such as thionyl chloride, in a suitable solvent, such as DCM, at a suitable temperature, such as 0° C.

Step 13: is a substitution reaction of a leaving group, such as chloride with a nucleophile, such as a methoxy group, using a suitable nucleophilic reagent, such as methanol, optionally in the presence of a suitable solvent, at a suitable temperature, such as room temperature.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006), incorporated herein by reference as it relates to such procedures.

Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by acid mediated cleavage (e.g. using an acid such as hydrochloric acid in 1,4-dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—C(O)CF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LC-MS.

General Experimental Details

All temperatures referred to are in ° C.

As used herein the symbols and conventions used in these processes, schemes and examples are consistent with those used in the contemporary scientific literature, for example, the *Journal of the American Chemical Society*. Unless otherwise noted, all starting materials were obtained from commercial suppliers and used without further purification. Specifically, the following abbreviations may be used in the examples and throughout the specification:

Abbreviations
ACD Advanced Chemistry Development, Inc.
AMU atomic mass unit
BOC/Boc tert-butyloxycarbonyl
cart cartridge
cat catalyst
CSH Water's Charged Surface Hybrid Technology
CV column volume
DCM dichloromethane
DIPEA diisopropylethylamine
DMAP 4-dimethylaminopyridine
DMF dimethylformamide
DMSO dimethylsulfoxide
DMSO-d$_6$ deuterated dimethylsulfoxide
dppf 1,1'-bis(diphenylphosphino)ferrocene
h hour(s)
HATU O-(7-azabenzotriazol-1-yl)-N,N,N',N'-tetramethyluronium hexafluorophosphate
IPA isopropyl alcohol
Isolera Biotage Flash purification system
LC liquid chromatography
LCMS liquid chromatography-mass spectrometry
M molar (concentration)
MDAP mass directed autopreparative chromatography
2-MeTHF 2-methyl tetrahydrofuran
min minute(s)
MS mass spectrometry
Ms-Cl methanesulfonyl chloride
MTBE methyl tert-butyl ether
N normal (concentration)
NMR nuclear magnetic resonance
NUT nuclear protein in testis
obs obscured
RBF round bottomed flask
Rt retention time
rt room temperature
sat saturated
SCX Isolute strong cation exchange sorbent SPE
sec second
SiO$_2$ silicon dioxide
SNAP Biotage (silica) flash chromatography cartridge
SP4 Biotage Flash purification system
SPE solid phase extraction
TFA trifluoroacetic acid
THF tetrahydrofuran
TLC thin layer chromatography
T3P propylphosphonic anhydride
UPLC ultra performance liquid chromatograpy
UV ultra-violet
wt weight The names of the following compounds have been obtained using the compound naming programme "ACD Name Pro 6.02" or using the naming functionality of ChemDraw Ultra 12.0.

LCMS Methodology
Formic Method
LC Conditions

The UPLC analysis was conducted on an Acquity UPLC CSH C18 column (50 mm×2.1 mm, i.d. 1.7 μm packing diameter) at 40° C.

The solvents employed were:
A=0.1% v/v solution of formic acid in water
B=0.1% v/v solution of formic acid in acetonitrile
The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time 0.27 sec
Inter scan delay 0.10 sec
High pH Method
LC Conditions The UPLC analysis was conducted on an Acquity UPLC CSH C18 column (50 mm×2.1 mm, i.d. 1.7 μm packing diameter) at 40° C.

The solvents employed were:
A=10 mM ammonium hydrogen carbonate in water adjusted to pH10 with ammonia solution
B=acetonitrile
The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
TFA Method
LC Conditions
The UPLC analysis was conducted on an Acquity UPLC CSH C18 column (50 mm×2.1 mm, i.d. 1.7 μm packing diameter) at 40° C.
The solvents employed were:
A=0.1% v/v solution of trifluoroacetic acid in water
B=0.1% v/v solution of trifluoroacetic acid in acetonitrile
The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
General MDAP Purification Methods
Listed below are examples of mass-directed autopreparative chromatography (MDAP) methods that have been used or may be used in compound purification.
MDAP (High pH). The HPLC analysis was conducted on an Xselect CSH C18 column (150 mm×30 mm i.d. 5 μm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 min.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (Formic). The HPLC analysis was conducted on an Xselect CSH C18 column (150 mm×30 mm i.d. 5 μm packing diameter) at ambient temperature, eluting with 0.1% formic acid in water (Solvent A) and 0.1% formic acid in acetonitrile (Solvent B) using an elution gradient of between 0 and 100% solvent B over 15 or 25 min.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.
MDAP (TFA). The HPLC analysis was conducted on an Xselect CSH C18 column (150 mm×30 mm i.d. 5 μm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 min.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.
NMR
Spectra were run on either a 400 MHz or 600 MHz NMR machine at either 302 K or at 392-393 K for VT spectra.

Intermediate 1: tert-Butyl 2-chloro-6-(methylcarbamoyl)isonicotinate

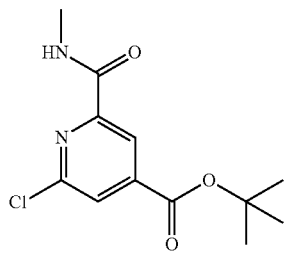 [SMILES: CNC(=O)c1cc(C(=O)OC(C)(C)C)cc(Cl)n1]

2,4,6-Tripropyl-1,3,5,2,4,6-trioxatriphosphinane 2,4,6-trioxide (40.7 g, 64.0 mmol) was added to a solution of 4-(tert-butoxycarbonyl)-6-chloropicolinic acid (15 g, 58.2 mmol, commercially available from, for example, Anichem) and Et$_3$N (16.23 mL, 116 mmol) in DCM (100 mL) at rt, then the mixture was stirred for 20 min before addition of methanamine (2M in THF, 38.8 mL, 78 mmol). The mixture was stirred for 2 h, then washed with water (100 mL) and saturated sodium bicarbonate solution, then dried and evaporated in vacuo to give a pale yellow gum. This was dissolved in DCM and loaded onto a 340 g silica column, then eluted with 0-40% EtOAc/cyclohexane and the product-containing fractions were evaporated in vacuo to give tert-butyl 2-chloro-6-(methylcarbamoyl)isonicotinate (6.9 g, 25.5 mmol, 43.8% yield) as a pale yellow gum which crystallised on standing.
LCMS (2 min High pH): Rt=1.16 min, [MH]$^+$=271.2.
$^1$H NMR (400 MHz, CDCl$_3$-d) δ ppm 8.55 (d, J=1.2 Hz, 1H) 7.95 (d, J=1.2 Hz, 1H) 7.79 (br. s, 1H) 3.05 (d, J=4.9 Hz, 3H) 1.61 (s, 9H)

Intermediate 2: 4-tert-Butyl 2-ethyl 6-(methylcarbamoyl)pyridine-2,4-dicarboxylate

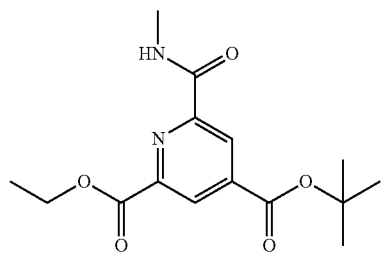 [SMILES: CCOC(=O)c1cc(C(=O)OC(C)(C)C)cc(C(=O)NC)n1]

tert-Butyl 2-chloro-6-(methylcarbamoyl)isonicotinate (4.2 g, 15.51 mmol) was dissolved in a mixture of DMF (50 mL) and ethanol (50 mL), then triethylamine (4.71 g, 46.5 mmol) and [(R)-(+)-2,2'-bis(diphenylphosphino)-1,1'-binaphthyl]palladium(II) chloride (0.621 g, 0.78 mmol) were added and the mixture was purged with carbon monoxide, then sealed and a balloon full of carbon monoxide fitted. The mixture was heated at 70° C. over the weekend, then evaporated in vacuo and the residue was partitioned between water (100 mL) and EtOAc (100 mL). The organic layer was washed with water (100 mL), dried and evaporated in vacuo. The dark brown residue was purified by chromatography on a 100 g silica column eluting with 0-50% EtOAc/cyclohexane to give 4-tert-butyl 2-ethyl 6-(methylcarbamoyl)pyridine-2,4-dicarboxylate (4.2 g, 13.62 mmol, 88% yield) as a pale yellow gum.

LCMS (2 min High pH): Rt=1.11 min, [MH]+=309.2.

$^1$H NMR (400 MHz, CDCl$_3$-d) δ ppm 8.80 (d, J=1.5 Hz, 1H), 8.67 (d, J=1.7 Hz, 1H), 8.08 (br. d, J=3.4 Hz, 1H), 4.50 (q, J=7.1 Hz, 2H), 3.08 (d, J=5.1 Hz, 3H), 1.63 (s, 9H), 1.46 (t, J=7.1 Hz, 3H)

Intermediate 3: tert-Butyl 2-(hydroxymethyl)-6-(methylcarbamoyl)isonicotinate

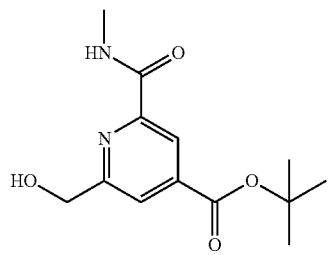 [SMILES: CNC(=O)c1cc(C(=O)OC(C)(C)C)cc(CO)n1]

Calcium chloride (4.54 g, 40.9 mmol) was added to a solution of 4-tert-butyl 2-ethyl 6-(methylcarbamoyl)pyridine-2,4-dicarboxylate (4.2 g, 13.62 mmol) in a mixture of ethanol (50 mL) and 2-MeTHF (50 mL) at 0° C., then sodium tetrahydroborate (0.773 g, 20.43 mmol) was added and the resulting red mixture was stirred for 2 h allowing the mixture to warm to rt. The mixture was allowed to stand overnight, then cooled in an ice bath and ammonium chloride solution (100 mL) was added slowly over 20 min. The mixture was extracted with EtOAc (2×150 mL), then the organics were dried and evaporated in vacuo and the residue purified by chromatography on a 50 g silica column to give tert-butyl 2-(hydroxymethyl)-6-(methylcarbamoyl)isonicotinate (2.2 g, 8.26 mmol, 61% yield) as a beige solid.

LCMS (2 min High pH): Rt=0.84 min, [MH]+=267.3.

$^1$H NMR (400 MHz, CDCl$_3$-d) δ ppm 8.49-8.58 (m, 1H), 7.90-8.02 (m, 2H), 4.87 (s, 2H), 3.05 (d, J=5.1 Hz, 3H), 1.61 (s, 9H). 1 exchangeable proton not observed.

Intermediate 4: tert-Butyl 2-(chloromethyl)-6-(methylcarbamoyl)isonicotinate

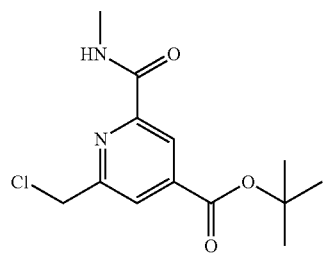 [SMILES: CNC(=O)c1cc(C(=O)OC(C)(C)C)cc(CCl)n1]

tert-Butyl 2-(hydroxymethyl)-6-(methylcarbamoyl)isonicotinate (1.5 g, 5.63 mmol) was dissolved in DCM (5 mL), sulfurous dichloride (1.26 mL, 16.90 mmol) was added and the reaction stirred at rt for 4 h, then the mixture was quenched by the addition of saturated sodium bicarbonate solution and the mixture was stirred for 20 min, then the organic layer was separated, dried and evaporated in vacuo to give tert-butyl 2-(chloromethyl)-6-(methylcarbamoyl)isonicotinate (1.35 g, 4.74 mmol, 84% yield) as a colourless solid.

LCMS (2 min High pH): Rt=1.13 min, [MH]+=285.2.

$^1$H NMR (400 MHz, CDCl$_3$-d) δ ppm 8.59 (d, J=1.2 Hz, 1H) 8.11 (d, J=1.2 Hz, 1H) 7.95 (br. s., 1H) 4.72 (s, 2H) 3.07 (d, J=5.1 Hz, 3H) 1.62 (s, 9H)

Intermediate 5: tert-Butyl 2-formyl-6-(methylcarbamoyl)isonicotinate

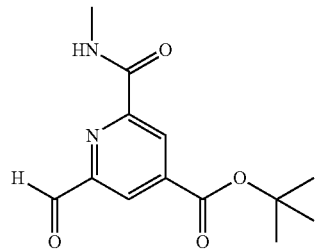 [SMILES: CNC(=O)c1cc(C(=O)OC(C)(C)C)cc(C=O)n1]

tert-Butyl 2-(hydroxymethyl)-6-(methylcarbamoyl)isonicotinate (543 mg, 2.04 mmol) was dissolved in DCM (5 mL). Dess-Martin periodinane (1009 mg, 2.38 mmol) was added and the mixture stirred at rt for 3 h. Sodium thiosulfate was added to the reaction mixture then NaHCO$_3$ was also added. The resultant mixture was stirred for 15 min. The aqueous phase was extracted with DCM three times and the combined organic layers were dried over MgSO$_4$ and evaporated. The crude product was purified by chromatography on SiO$_2$ (Biotage SNAP 10 g, eluting with 0-50% ethyl acetate/cyclohexane). The desired fractions were concentrated to give tert-butyl 2-formyl-6-(methylcarbamoyl)isonicotinate (501 mg, 1.71 mmol, 84% yield) as a colourless oil.

LCMS (2 min Formic): Rt=0.97 min, [MH]⁺=265.3.

¹H NMR (400 MHz, CDCl₃-d) δ ppm 10.14 (s, 1H), 8.88 (d, J=1.5 Hz, 1H), 8.55 (d, J=1.5 Hz, 1H), 8.00 (br. s., 1H), 3.12 (d, J=4.9 Hz, 3H), 1.62-1.66 (m, 9H)

Intermediate 6: tert-Butyl 2-benzyl-6-(methylcarbamoyl)isonicotinate

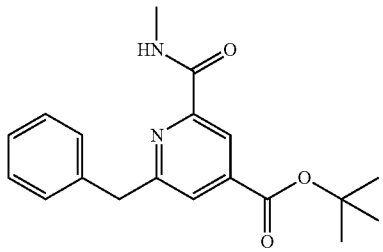 [SMILES: CNC(=O)c1cc(C(=O)OC(C)(C)C)cc(Cc2ccccc2)n1]

tert-Butyl 2-chloro-6-(methylcarbamoyl)isonicotinate (5 g, 18.47 mmol, commercially available from, for example, Anichem) and PdCl₂(PPh₃)₂ (1.296 g, 1.85 mmol) were dissolved in THF (50 mL) and benzylzinc(II) bromide (0.5M in THF, 55.4 mL, 27.7 mmol) was added, then the mixture was heated at 70° C. for 2 h. The solvent was evaporated in vacuo and the residue purified by chromatography on a 100 g silica column eluting with 0-50% EtOAc/cyclohexane to give tert-butyl 2-benzyl-6-(methylcarbamoyl)isonicotinate (5.7 g, 17.46 mmol, 95% yield) as a dark brown oil which was used in the next step without further purification.

LCMS (2 min High pH): Rt=1.30 min, [MH]⁺=327.3.

1H NMR (400 MHz, CDCl₃) δ ppm 8.46 (d, J=1.2 Hz, 1H), 7.91-8.07 (m, 1H), 7.78 (d, J=1.2 Hz, 1H), 7.28-7.34 (m, 2H), 7.21-7.27 (m, 3H), 4.21 (s, 2H) 3.05 (d, J=5.1 Hz, 3H), 1.58 (s, 9H)

Intermediate 7: 2-Benzyl-6-(methylcarbamoyl)isonicotinic acid

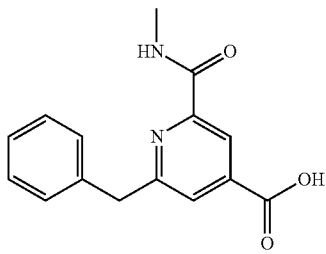 [SMILES: CNC(=O)c1cc(C(=O)O)cc(Cc2ccccc2)n1]

tert-Butyl 2-benzyl-6-(methylcarbamoyl)isonicotinate (2.5 g, 7.66 mmol) was dissolved in DCM (30 mL), then TFA (10 mL, 130 mmol) was added and the mixture was stirred for 3 h at rt. The solvent was evaporated in vacuo to give a pale yellow gum. The crude material was dissolved in DCM (100 mL) and washed with water (100 mL), the organic layer was dried and evaporated in vacuo to give 2-benzyl-6-(methylcarbamoyl)isonicotinic acid (2.0 g, 7.40 mmol, 97% yield) as a pale yellow solid LCMS (2 min High pH): Rt=0.63 min, [MH]⁺=271.3.

¹H NMR (400 MHz, DMSO-d6) δ ppm 13.76 (br. s., 1H), 8.73 (d, J=4.9 Hz, 1H), 8.24 (d, J=1.5 Hz, 1H), 7.83 (d, J=1.5 Hz, 1H), 7.34-7.39 (m, 2H), 7.28-7.34 (m, 2H) 7.19-7.25 (m, 1H), 4.26 (s, 2H), 2.87 (d, J=4.6 Hz, 3H)

Intermediate 8: (+/−)-tert-Butyl 2-(methylcarbamoyl)-6-(1-phenylethyl)isonicotinate

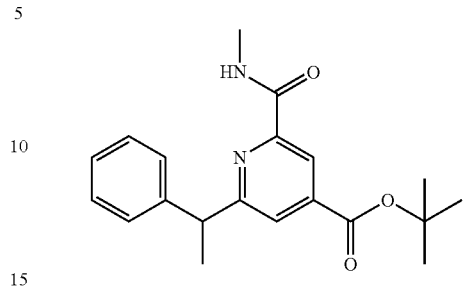

tert-Butyl 2-chloro-6-(methylcarbamoyl)isonicotinate (0.5 g, 1.85 mmol) was dissolved in THF (20 mL) and palladium dichloride bis triphenylphosphine (0.130 g, 0.19 mmol) was added. The solution was sparged with nitrogen for 5 min, then (1-phenylethyl)zinc(II) bromide (0.5M in THF, 7.39 mL, 3.69 mmol, commercially available from, for example, Sigma Aldrich) was added and the mixture heated at 70° C. for 2 h. The solution was diluted with EtOAc (100 mL) and washed with water (100 mL), dried and evaporated in vacuo. The residue was purified by chromatography on a 25 g silica column eluting with 0-50% EtOAc/cyclohexane and the product-containing fractions evaporated in vacuo to give tert-butyl 2-(methylcarbamoyl)-6-(1-phenylethyl)isonicotinate (0.41 g, 1.20 mmol, 65% yield) as a dark yellow oil.

LCMS (2 min High pH): Rt=1.37 min, [MH]⁺=341.3.

¹H NMR (400 MHz, CDCl₃-d) δ ppm 8.45 (d, J=1.5 Hz, 1H), 8.02 (br. s., 1H), 7.81 (d, J=1.2 Hz, 1H), 7.18-7.36 (obs. m, 5H), 4.38 (q, J=7.3 Hz, 1H), 3.07 (d, J=5.1 Hz, 3H), 1.74 (d, J=7.3 Hz, 3H), 1.59 (s, 9H)

Intermediate 9: (+/−)-2-(Methylcarbamoyl)-6-(1-phenylethyl)isonicotinic acid

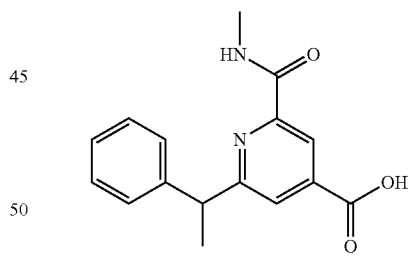

tert-Butyl 2-(methylcarbamoyl)-6-(1-phenylethyl)isonicotinate (0.41 g, 1.20 mmol) was dissolved in TFA (6 mL) and stirred for 3 h at rt, then the mixture was evaporated in vacuo and the residue partitioned between water (20 mL) and DCM (20 mL). The organic layer was dried and evaporated in vacuo to give 2-(methylcarbamoyl)-6-(1-phenylethyl)isonicotinic acid (305 mg, 1.07 mmol, 89% yield) as a grey foam.

LCMS (2 min High pH): Rt=0.69 min, [MH]⁺=285.2.

¹H NMR (400 MHz, DMSO-d6) δ ppm 13.74 (br. s., 1H), 8.75 (m, J=4.9 Hz, 1H), 8.21 (d, J=1.5 Hz, 1H) 7.82 (d, J=1.5 Hz, 1H), 7.42 (br. d, J=7.1 Hz, 2H), 7.30 (t, J=7.5 Hz, 2H), 7.16-7.23 (m, 1H), 4.47 (q, J=7.1 Hz, 1H), 2.89 (d, J=4.9 Hz, 3H), 1.72 (d, J=7.3 Hz, 3H)

Intermediate 10: (R)-tert-Butyl 2-(methylcarbamoyl)-6-(1-phenylethyl)isonicotinate Intermediate 11: (S)-tert-Butyl 2-(methylcarbamoyl)-6-(1-phenylethyl)isonicotinate

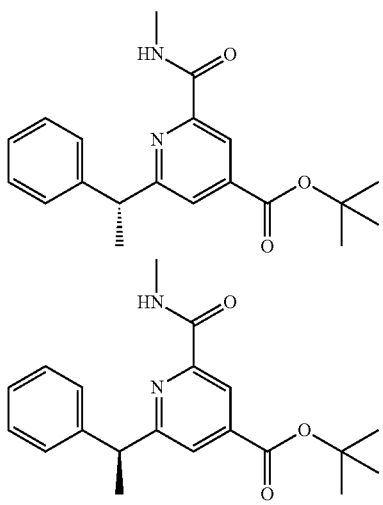

(+/−)-tert-Butyl 2-(methylcarbamoyl)-6-(1-phenylethyl)isonicotinate (7.78 g) was purified by chiral HPLC. The racemate was dissolved in EtOH (150 mL). Injection: 1.1 mL of the solution was injected via preparative autosampler, onto the column (20% EtOH/heptane+0.2% isopropylamine, flow rate=42.5 mL/min, detection wavelength=280 nm, band width 140 nm, reference 400 nm bandwidth 100 nm, Column 30 mm×25 cm Chiralcel OJ-H). Fractions from 11.2-13.7 min were bulked and labelled peak 1. Fractions from 15.7-19 min were bulked and labelled peak 2. The bulked fractions were concentrated in vacuo and then transferred to weighed flasks.

The fractions corresponding to peak 1 were collected to afford intermediate 10 (2.84 g)

LCMS (2 min High pH): Rt=1.35 min, [MH]⁺=341.3

The fractions corresponding to peak 2 were collected to afford intermediate 11 (2.80 g)

LCMS (2 min High pH): Rt=1.35 min, [MH]⁺=341.3

$^1$H NMR (400 MHz, CDCl$_3$) δ ppm 8.46 (d, J=1.2 Hz, 1H), 8.03 (br. s., 1H), 7.82 (d, J=1.5 Hz, 1H), 7.20-7.36 (m, 5H), 4.39 (q, J=7.2 Hz, 1H), 3.08 (d, J=5.1 Hz, 3H), 1.76 (d, J=7.1 Hz, 3H), 1.60 (s, 9H)

Intermediate 12: (S)-2-(Methylcarbamoyl)-6-(1-phenylethyl)isonicotinic acid

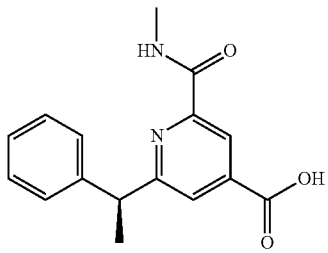 [SMILES: CNC(=O)c1cc(C(=O)O)cc([C@@H](C)c2ccccc2)n1]

A mixture of (S)-tert-butyl 2-(methylcarbamoyl)-6-(1-phenylethyl)isonicotinate (2.19 g, 6.43 mmol, intermediate 11) and trifluoroacetic acid (10 mL, 130 mmol) in DCM (15 mL) was stirred at rt for 19 h. The volatiles were evaporated from the mixture in vacuo and the oily residue redissolved in acetonitrile (ca. 10 mL) and the solvent evaporated in vacuo. The orange oily residue had ether (ca. 10 mL) added and a white solid precipitated. The solid was filtered, washed with ether (2×5 mL) and dried in vacuo to give the desired product as a white solid; (S)-2-(methylcarbamoyl)-6-(1-phenylethyl)isonicotinic acid (1.18 g, 4.14 mmol, 64% yield)

The solvent from the mother liquor of the second ether wash was evaporated under a stream of nitrogen to give a second batch of the desired product as a white solid; (S)-2-(methylcarbamoyl)-6-(1-phenylethyl)isonicotinic acid (95.6 mg, 0.336 mmol, 5.23% yield)

The solvent from the combined mother liquors of the initial trituration and first ether wash were evaporated under a stream of nitrogen and the orange viscous oil which resulted was triturated with ether (5 mL). The mother liquor was decanted away and the solid triturated with further ether (3×5 mL), each time decanting the mother liquor. The solid was dried in vacuo to give a third batch of the desired product as a cream solid, yield; (S)-2-(methylcarbamoyl)-6-(1-phenylethyl)isonicotinic acid (310.8 mg, 1.09 mmol, 17% yield)

The combined mother liquors from the isolation of the above batch were evaporated under a stream of nitrogen and the resultant orange semi-crystalline solid was washed with ether (3 mL). The mother liquor was decanted away and the solid triturated with further ether (3×3 mL), each time decanting the mother liquor. The solid was dried in vacuo to give a fourth batch of the desired product as a cream solid (100.4 mg)

Total product isolated summed over the four batches=1.68 g, 92%.

LCMS (2 min Formic): Rt=1.00 min, [MH]⁺=285.3

$^1$H NMR (400 MHz, DMSO-d6) δ ppm 13.81 (br. s., 1H), 8.80 (q, J=4.5 Hz, 1H), 8.22 (s, 1H), 7.83 (d, J=1.5 Hz, 1H), 7.43 (d, J=7.1 Hz, 2H), 7.27-7.34 (m, 2H), 7.16-7.24 (m, 1H), 4.48 (q, J=7.3 Hz, 1H), 2.90 (d, J=4.9 Hz, 3H), 1.73 (d, J=7.3 Hz, 3H)

Intermediate 13: (R)-2-(Methylcarbamoyl)-6-(1-phenylethyl)isonicotinic acid

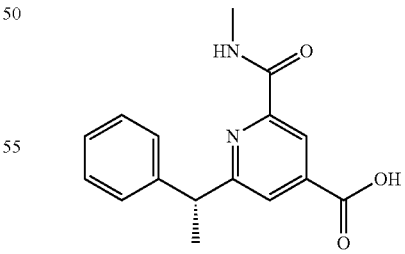

(R)-tert-Butyl 2-(methylcarbamoyl)-6-(1-phenylethyl)isonicotinate (497 mg, 1.46 mmol, intermediate 10) was taken up in DCM (5 mL), TFA (0.5 mL, 6.49 mmol) was added and the reaction left to stir at rt overnight. TFA (0.5 mL, 6.49 mmol) was added again and the reaction was refluxed at 50° C. for 3 h. More TFA (1 mL) was added to the reaction, which was then left to stir for a further 2 h. The reaction was concentrated in vacuo. The sample was loaded in methanol and purified by SPE on sulphonic acid (SCX, 2 g) and eluted through with methanol. The appropriate fractions were combined and evaporated in vacuo to give the required product (350 mg) as a pink solid.

LCMS (2 min High pH): Rt=0.68 min, [MH]⁺=285.2.

Intermediate 14: tert-Butyl 2-((1H-indol-4-yl)methyl)-6-(methylcarbamoyl)isonicotinate

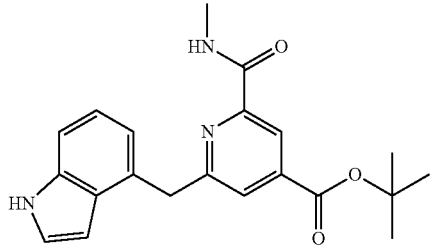 [SMILES: CNC(=O)c1cc(C(=O)OC(C)(C)C)cc(Cc2cccc3[nH]ccc23)n1]

tert-Butyl 2-(chloromethyl)-6-(methylcarbamoyl)isonicotinate (100 mg, 0.35 mmol) was combined with (1H-indol-4-yl)boronic acid (113 mg, 0.70 mmol), potassium carbonate (291 mg, 2.107 mmol) and PdCl₂(dppf) (51.4 mg, 0.07 mmol) in 1,4-dioxane (1 mL) and water (0.5 mL) in a 2 mL microwave vial. This was heated at 120° C. for 40 min. The solution was filtered though celite eluting with EtOAc (10 mL) then dried and concentrated. The crude product was purified by chromatography on SiO₂ (Biotage SNAP 10 g, eluting with 0-60% ethyl acetate/cyclohexane). The desired fractions were concentrated to give tert-butyl 2-((1H-indol-4-yl)methyl)-6-(methylcarbamoyl)isonicotinate (75.4 mg, 0.17 mmol, 47% yield) as a white solid.

LCMS (2 min Formic): Rt=1.20 min, [MH]+=366.2.

¹H NMR (400 MHz, MeOH-d4) δ ppm 8.30 (d, J=1.2 Hz, 1H), 7.76 (d, J=1.2 Hz, 1H), 7.31 (d, J=8.3 Hz, 1H), 7.21 (d, J=3.2 Hz, 1H), 7.03-7.11 (m, 1H), 6.91 (br. d, J=7.1 Hz, 1H), 6.47 (dd, J=3.2, 0.7 Hz, 1H), 4.52 (s, 2H) 2.99 (s, 3H), 1.54 (s, 9H). Exchangeables not observed.

Intermediate 15: 2-((1H-Indol-4-yl)methyl)-6-(methylcarbamoyl)isonicotinic acid

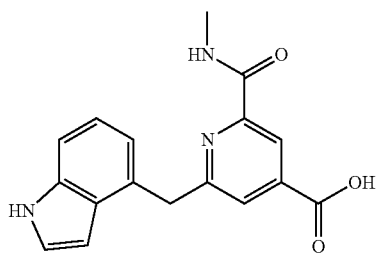 [SMILES: CNC(=O)c1cc(C(=O)O)cc(Cc2cccc3[nH]ccc23)n1]

To a solution of tert-butyl 2-((1H-indol-4-yl)methyl)-6-(methylcarbamoyl)isonicotinate (75.4 mg, 0.17 mmol) in DCM (3 mL) was added TFA (0.60 mL, 7.79 mmol) and the reaction mixture was stirred at rt overnight. Further TFA (0.3 mL, 0.17 mmol) was added and the resultant mixture stirred for 3 h. The reaction mixture was concentrated in vacuo to give 2-((1H-indol-4-yl)methyl)-6-(methylcarbamoyl)isonicotinic acid (184 mg, 0.15 mmol, 90% yield, ~25% purity).

LCMS (2 min Formic): Rt=0.88 min, [MH]+=310.1.

¹H NMR (400 MHz, DMSO-d₆) δ ppm 11.59-12.89 (m, 1H), 11.11 (br. s., 1H), 8.76 (d, J=4.9 Hz, 1H), 8.19 (d, J=1.2 Hz, 1H), 7.71 (d, J=1.5 Hz, 1H), 7.21-7.39 (m, 2H), 7.05 (t, J=7.6 Hz, 1H), 6.95 (d, J=6.8 Hz, 1H), 6.46-6.56 (m, 1H), 4.48 (s, 2H), 2.88 (d, J=4.9 Hz, 3H).

Intermediate 16: (+/−)-tert-Butyl 2-(hydroxy(phenyl)methyl)-6-(methylcarbamoyl)isonicotinate

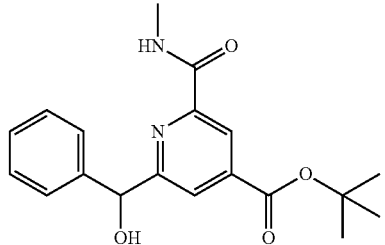 [SMILES: CNC(=O)c1cc(C(=O)OC(C)(C)C)cc(C(O)c2ccccc2)n1]

To a solution of tert-butyl 2-formyl-6-(methylcarbamoyl)isonicotinate (118 mg, 0.45 mmol) in THF (1.5 mL) at 0° C., was added dropwise phenylmagnesium bromide (1M in THF, 2 mL, 2 mmol). The reaction mixture was stirred for 2 h. The reaction mixture was poured onto a saturated ammonium chloride aqueous solution and extracted with EtOAc (20 mL×3). The organic layer was dried over MgSO₄ and concentrated in vacuo. The crude product was purified by chromatography on SiO₂ (Biotage SNAP 10 g, eluting with 0-60% ethyl acetate/cyclohexane). The desired fractions were concentrated to give tert-butyl 2-(hydroxy(phenyl)methyl)-6-(methylcarbamoyl)isonicotinate (43 mg, 0.11 mmol, 24% yield).

LCMS (2 min Formic): Rt=1.09 min, [MH]⁺=343.3.

¹H NMR (400 MHz, MeOH-d4) δ ppm 8.38 (d, J=1.2 Hz, 1H) 8.05 (d, J=1.2 Hz, 1H) 7.42-7.47 (m, 2H) 7.22-7.36 (m, 3H) 5.95 (s, 1H) 2.99 (s, 3H) 1.60 (s, 9H). Exchangeables not observed.

Intermediate 17: (+/−)-2-(Hydroxy(phenyl)methyl)-6-(methylcarbamoyl)isonicotinic acid

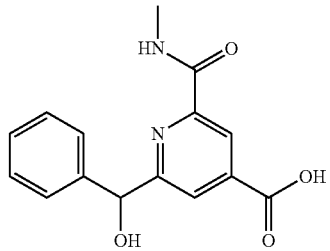 [SMILES: CNC(=O)c1cc(C(=O)O)cc(C(O)c2ccccc2)n1]

To a solution of tert-butyl 2-(hydroxy(phenyl)methyl)-6-(methylcarbamoyl)isonicotinate (43 mg, 0.13 mmol) in DCM (0.5 mL) was added TFA (0.4 mL, 5.19 mmol) and the reaction mixture was stirred for 2 h and then overnight. Further TFA (0.4 mL, 0.13 mmol) was added and the reaction mixture was stirred for 5 h, then the solvent was removed to give 2-(hydroxy(phenyl)methyl)-6-(methylcarbamoyl)isonicotinic acid (47.9 mg, 0.12 mmol, 93% yield, 70% purity) which was used directly in the next step.

LCMS (2 min Formic): Rt=0.74 min, [MH]⁺=287.1.
¹H NMR (400 MHz, MeOH-d4) δ ppm 8.45 (d, J=1.2 Hz, 1H), 8.10 (d, J=1.5 Hz, 1H), 7.41-7.48 (m, 2H), 7.21-7.38 (m, 3H), 5.97 (s, 1H), 2.99 (s, 3H). Exchangeables not observed.

Intermediate 18: (+/−)-tert-Butyl 2-(chloro(phenyl)methyl)-6-(methylcarbamoyl)isonicotinate

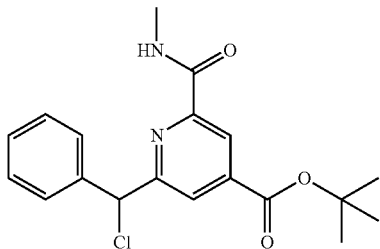 [SMILES: CNC(=O)c1cc(C(=O)OC(C)(C)C)cc(C(Cl)c2ccccc2)n1]

To a solution of tert-butyl 2-(hydroxy(phenyl)methyl)-6-(methylcarbamoyl)isonicotinate (46 mg, 0.13 mmol) in DCM (4 mL) at 0° C., was added dropwise thionyl chloride (30 μL, 0.41 mmol). The reaction mixture was then stirred at rt for 12 h. Further thionyl chloride (50 μL, 0.69 mmol) was added and the resultant mixture was stirred for 5 h then concentrated in vacuo to give tert-butyl 2-(chloro(phenyl)methyl)-6-(methylcarbamoyl)isonicotinate (54 mg) which was used without purification in the subsequent reaction.
LCMS (2 min Formic): Rt=1.33 min, [MH]⁺=361.1

Intermediate 19: (+/−)-tert-Butyl 2-(methoxy(phenyl)methyl)-6-(methylcarbamoyl)isonicotinate

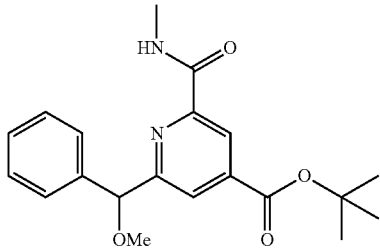 [SMILES: CNC(=O)c1cc(C(=O)OC(C)(C)C)cc(C(OC)c2ccccc2)n1]

A solution of tert-butyl 2-(chloro(phenyl)methyl)-6-(methylcarbamoyl)isonicotinate (54 mg, 0.15 mmol) in methanol (5 mL) was stirred over the weekend. The reaction mixture was then heated under reflux for 1 h initially, then 4 h and finally overnight. The reaction mixture was then concentrated in vacuo. The resultant crude product was purified by flash silica chromatography (SNAP 10 g cartridge, eluent: 0-50% ethyl acetate/cyclohexane). The desired fractions were combined and concentrated in vacuo to give tert-butyl 2-(methoxy(phenyl)methyl)-6-(methylcarbamoyl)isonicotinate (33 mg, 0.08 mmol, 56% yield) as a colourless oil.
LCMS (2 min Formic): Rt=1.26 min, [MH]⁺=357.2.
¹H NMR (400 MHz, MeOH-d4) δ ppm 8.38 (d, J=1.5 Hz, 1H), 8.10 (d, J=1.5 Hz, 1H), 7.44 (d, J=7.3 Hz, 2H), 7.30-7.38 (m, 2H) 7.23-7.30 (m, 1H), 5.54 (s, 1H), 3.44 (s, 3H), 2.98 (s, 3H), 1.61 (s, 9H). Exchangeable proton not observed.

Intermediate 20: (+/−)-2-(Methoxy(phenyl)methyl)-6-(methylcarbamoyl)isonicotinic acid

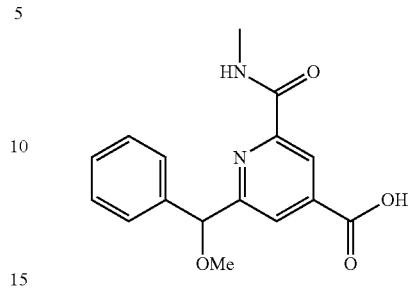

To a solution of tert-butyl 2-(methoxy(phenyl)methyl)-6-(methylcarbamoyl)isonicotinate (33 mg, 0.09 mmol) in DCM (1 mL) was added 2,2,2-trifluoroacetic acid (0.5 mL, 6.49 mmol) and the reaction mixture was stirred overnight. This was then washed with water and extracted with DCM three times, then it was dried. The solvent was removed in vacuo to give 2-(methoxy(phenyl)methyl)-6-(methylcarbamoyl)isonicotinic acid (44.9 mg, 0.09 mmol, 97% yield, ~60% purity)
LCMS (2 min Formic): Rt=0.91 min, [MH]⁺=301.1
¹H NMR (400 MHz, MeOH-d4) δ ppm 8.45 (d, J=1.2 Hz, 1H), 8.17 (d, J=1.5 Hz, 1H), 7.98 (br. s, 1H), 7.42-7.49 (m, 2H), 7.31-7.38 (m, 2H), 7.27 (m, J=7.3 Hz, 1H), 5.55 (s, 1H) 3.45 (s, 3H), 2.99 (d, J=3.2 Hz, 3H). 1 exchangeable proton not observed.

EXAMPLES

Example 1: 6-Benzyl-N²-methyl-N⁴-propylpyridine-2,4-dicarboxamide

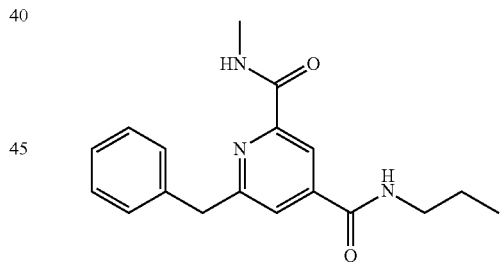

2-Benzyl-6-(methylcarbamoyl)isonicotinic acid (50 mg, 0.19 mmol), HATU (105 mg, 0.28 mmol), DIPEA (0.1 mL, 0.57 mmol), propan-1-amine (0.03 mL, 0.37 mmol) and DMF (1 mL) were stirred at rt under N₂. After stirring for 45 min the solution was concentrated to give an orange oil (250 mg). This was purified by chromatography on SiO₂ (Biotage SNAP 25 g cartridge, eluting with 30-100% ethylacetate/cyclohexane. The appropriate fractions were concentrated to give 6-benzyl-N²-methyl-N⁴-propylpyridine-2,4-dicarboxamide (28 mg, 0.081 mmol, 44% yield) as a colourless oil.
LCMS (2 min Formic): Rt=0.98 min, [MH]+=312.0.
The following examples were prepared in a similar manner to example 1 from intermediate 7, 2-benzyl-6-(methylcarbamoyl)isonicotinic acid and the appropriate commercially available amine monomer, to provide the listed examples.

EXAMPLES

| Ex No. | Name | Structure | Mass (mg) | Yield (%) | [MH]+ | Rt (min) |
|---|---|---|---|---|---|---|
| 2 | 6-Benzyl-$N^2$,$N^4$-dimethylpyridine-2,4-dicarboxamide | 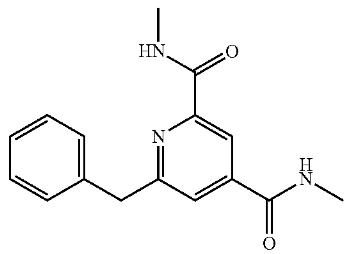 [SMILES: CNC(=O)c1cc(Cc2ccccc2)nc(C(=O)NC)c1] | 74.8 | 89 | 284.1 | 0.83 (formic) |
| 3 | (+/−)-6-Benzyl-$N^4$-(3-hydroxybutyl)-$N^2$-methylpyridine-2,4-dicarboxamide | 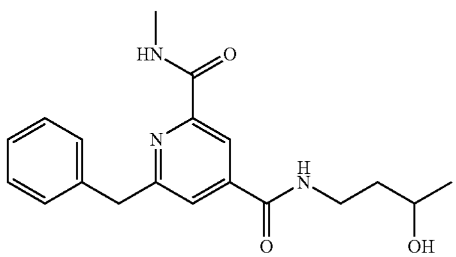 [SMILES: CNC(=O)c1cc(C(=O)NCCC(C)O)cc(Cc2ccccc2)n1] | 10.6 | 28 | 342 | 0.83 (High pH) |
| 4 | $N^4$-(2-(1H-Imidazol-5-yl)ethyl)-6-benzyl-$N^2$-methylpyridine-2,4-dicarboxamide | 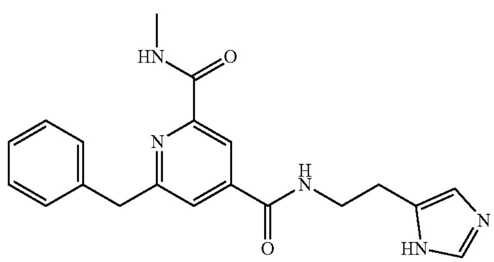 [SMILES: CNC(=O)c1cc(C(=O)NCCc2cnc[nH]2)cc(Cc2ccccc2)n1] | 10.5 | 26 | 364 | 0.56 (High pH) |
| 5 | 6-Benzyl-$N^4$-(3-hydroxypropyl)-$N^2$-methylpyridine-2,4-dicarboxamide | 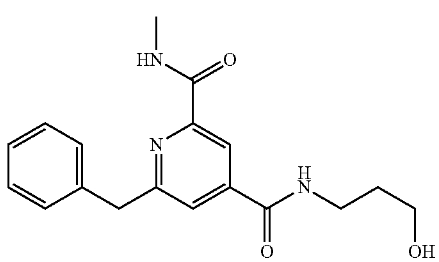 [SMILES: CNC(=O)c1cc(C(=O)NCCCO)cc(Cc2ccccc2)n1] | 9.1 | 25 | 328 | 0.79 (High pH) |
| 7 | 6-Benzyl-$N^4$-(3-methoxypropyl)-$N^2$-methylpyridine-2,4-dicarboxamide | 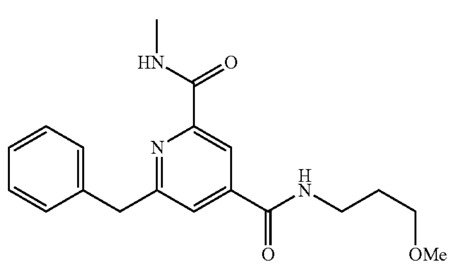 [SMILES: CNC(=O)c1cc(C(=O)NCCCOC)cc(Cc2ccccc2)n1] | 11.7 | 31 | 342 | 0.91 (High pH) |

-continued

| Ex No. | Name | Structure | Mass (mg) | Yield (%) | [MH]+ | Rt (min) |
|---|---|---|---|---|---|---|
| 8 | N4-(2-(1H-Pyrazol-3-yl)ethyl)-6-benzyl-N2-methylpyridine-2,4-dicarboxamide | 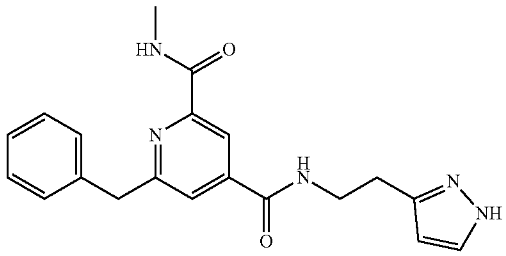 [SMILES: CNC(=O)c1cc(C(=O)NCCc2cc[nH]n2)cc(Cc2ccccc2)n1] | 11.2 | 25 | 364 | 0.82 (High pH) |
| 9 | 6-Benzyl-N4-isopentyl-N2-methylpyridine-2,4-dicarboxamide | 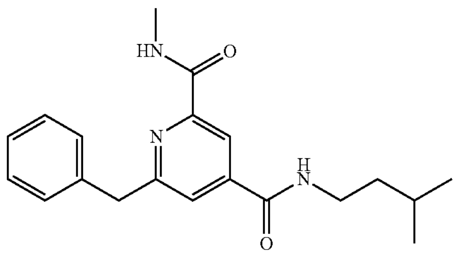 | 61.6 | 90 | 340.3 | 1.15 (High pH) |
| 10 | 6-Benzyl-N2-methyl-N4-(oxazol-2-yl)pyridine-2,4-dicarboxamide | 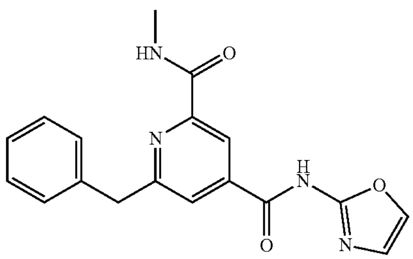 [SMILES: CNC(=O)c1cc(C(=O)Nc2ncco2)cc(Cc2ccccc2)n1] | 40.3 | 61 | 337.2 | 0.87 (formic) |
| 13 | 6-Benzyl-N2-methyl-N4-(1H-pyrazol-5-yl)pyridine-2,4-dicarboxamide | 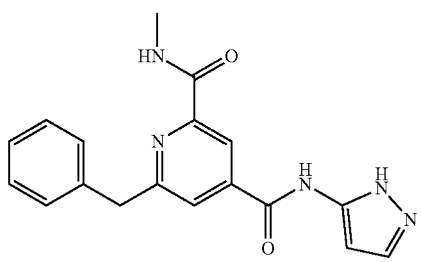 [SMILES: CNC(=O)c1cc(C(=O)Nc2ccn[nH]2)cc(Cc2ccccc2)n1] | 23.1 | 36 | 336.3 | 0.88 (High pH) |
| 20 | N4-((1H-Pyrazol-3-yl)methyl)-6-benzyl-N2-methylpyridine-2,4-dicarboxamide | 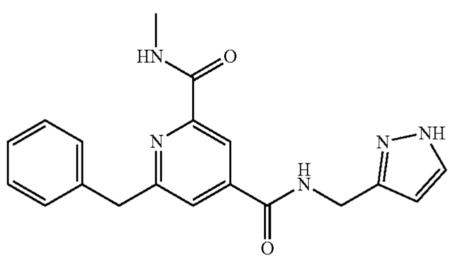 [SMILES: CNC(=O)c1cc(C(=O)NCc2cc[nH]n2)cc(Cc2ccccc2)n1] | 8.7 | 13 | 350.2 | 0.83 (formic) |
| 24 | 6-Benzyl-N2-methyl-N4-((1-methyl-1H-pyrazol-4-yl)methyl)pyridine-2,4-dicarboxamide | 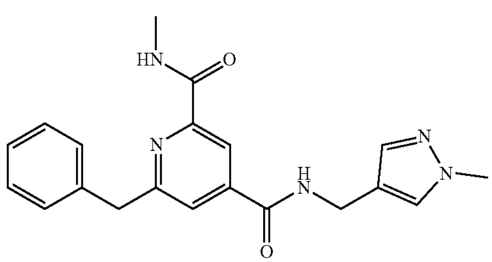 [SMILES: CNC(=O)c1cc(C(=O)NCc2cnn(C)c2)cc(Cc2ccccc2)n1] | 80 | 57 | 364.3 | 0.88 (high pH) |

| Ex No. | Name | Structure | Mass (mg) | Yield (%) | [MH]+ | Rt (min) |
|---|---|---|---|---|---|---|
| 28 | 6-Benzyl-$N^2$-methyl-$N^4$-(1-methyl-1H-pyrazol-3-yl)pyridine-2,4-dicarboxamide | 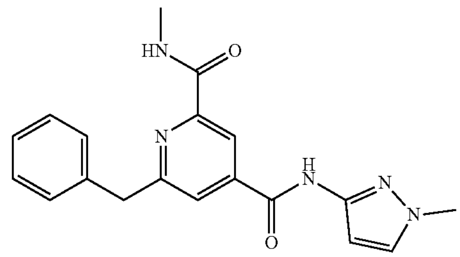 [SMILES: CNC(=O)c1cc(C(=O)Nc2ccn(C)n2)cc(Cc2ccccc2)n1] | 63.8 | 91 | 350.3 | 0.94 (high pH) |
| 30 | 6-Benzyl-$N^4$-(3,3-diethoxypropyl)-$N^2$-methylpyridine-2,4-dicarboxamide | 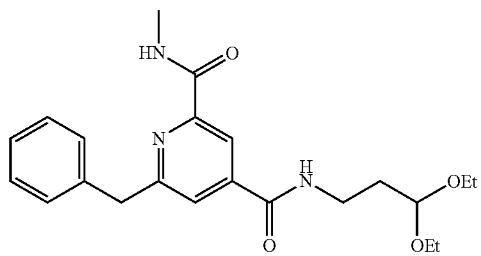 [SMILES: CCOC(CCNC(=O)c1cc(Cc2ccccc2)nc(C(=O)NC)c1)OCC] | 91.3 | 79 | 400.4 | 1.08 (High pH) |
| 34 | 6-Benzyl-$N^4$-(4,4-diethoxybutyl)-$N^2$-methylpyridine-2,4-dicarboxamide | 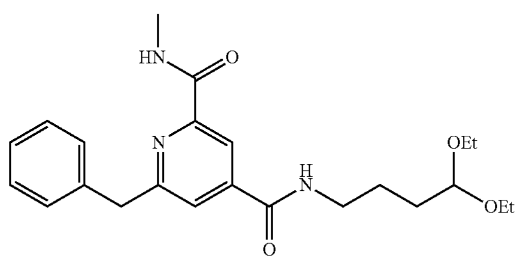 [SMILES: CCOC(CCCNC(=O)c1cc(Cc2ccccc2)nc(C(=O)NC)c1)OCC] | 651 | 82 | 368.3 | 1.08 (formic) |
| 51 | 6-Benzyl-$N^4$-(1-(2-hydroxyethyl)-1H-pyrazol-3-yl)-$N^2$-methylpyridine-2,4-dicarboxamide | 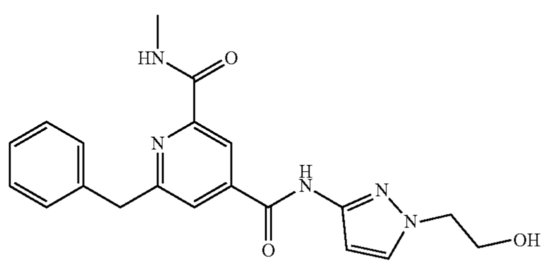 [SMILES: CNC(=O)c1cc(C(=O)Nc2ccn(CCO)n2)cc(Cc2ccccc2)n1] | 40.5 | 56 | 380.4 | 0.86 (high pH) |

Example 6: (+/−)-$N^4$-(2-Hydroxyethyl)-$N^2$-methyl-6-(1-phenylethyl)pyridine-2,4-dicarboxamide

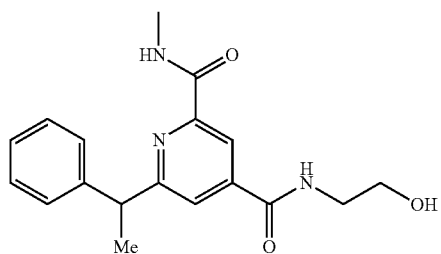 [SMILES: CNC(=O)c1cc(C(=O)NCCO)cc(C(C)c2ccccc2)n1]

2-(Methylcarbamoyl)-6-(1-phenylethyl)isonicotinic acid (50 mg, 0.18 mmol) was taken up in DMF (2 mL), DIPEA (0.092 mL, 0.53 mmol) was added, shortly followed by HATU (100 mg, 0.26 mmol) and the reaction left to stir at rt for 10 min. 2-Aminoethanol (0.011 mL, 0.18 mmol) was added and the reaction was left to stir for a further 1 h. The mixture was concentrated in vacuo. The residue was dissolved in ethyl acetate (10 mL) before being washed with sodium bicarbonate solution (10 mL). The aqueous layer was washed with ethyl acetate (10 mL). The combined organic layers were then washed with brine (10 mL) before being dried over sodium sulfate and filtered through a hydrophobic frit. The reaction was then concentrated in vacuo. The crude product was dissolved in 1:1 MeOH:DMSO (0.8 mL) and purified by MDAP (high pH). The MDAP failed to collect the products and the product was instead collected with the waste solvent. The waste material was evaporated in vacuo. The crude product was dissolved in DMSO and 1:1 DMSO:MeOH (0.3 mL) and purified by MDAP (high pH). The solvent was evaporated in vacuo to give the title compound (5.9 mg).

LCMS (2 min High pH): Rt=0.87 min, [MH]+=328.2.

Example 11: 6-Benzyl-N²-methyl-N⁴-(1-methyl-1H-pyrazol-4-yl)pyridine-2,4-dicarboxamide

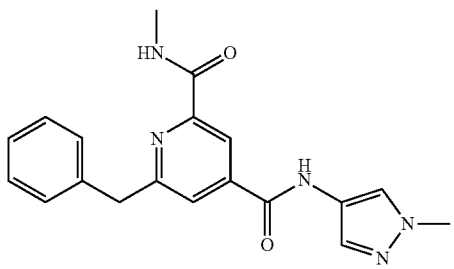 [SMILES: CNC(=O)c1cc(C(=O)Nc2cnn(C)c2)cc(Cc2ccccc2)n1]

To a mixture of 1-methyl-1H-pyrazol-4-amine, hydrochloride (33.0 mg, 0.25 mmol), HATU (92.8 mg, 0.24 mmol) and DIPEA (0.100 mL, 0.57 mmol) in DMF (1 mL) was added 2-benzyl-6-(methylcarbamoyl)isonicotinic acid (50.9 mg, 0.19 mmol). This mixture was stirred at rt for 30 min. The mixture was evaporated under a stream of nitrogen and the resulting sticky dark brown solid redissolved in DMSO (2 mL) and directly purified by MDAP (2×1 mL injection, high pH). The required fractions (fraction 1 for both runs) were evaporated under a stream of nitrogen, redissolved in methanol (approx. 2 mL) and dichloromethane (approx. 2 mL) and combined. This solution was evaporated under a stream of nitrogen and the residue dried in vacuo to give the desired product as a light pink glassy solid—6-benzyl-N²-methyl-N⁴-(1-methyl-1H-pyrazol-4-yl)pyridine-2,4-dicarboxamide (51.9 mg, 0.15 mmol, 79% yield).

LCMS (2 min High pH): Rt=0.91 min, [MH]+=350.3.

¹H NMR (400 MHz, DMSO-d₆) δ ppm 10.89 (s, 1H) 8.78 (br. q, J=4.6, 4.6, 4.6 Hz, 1H), 8.39 (s, 1H), 8.04 (s, 1H), 7.90 (d, J=0.7 Hz, 1H), 7.59 (s, 1H) 7.38 (br. d, J=6.8 Hz, 2H), 7.32 (t, J=7.5 Hz, 2H), 7.22 (br. t, J=7.3, 7.3 Hz, 1H), 4.25 (s, 2H) 3.82 (s, 3H), 2.88 (d, J=4.9 Hz, 3H)

Example 12: 6-Benzyl-N²-methyl-N⁴-(1H-pyrazol-4-yl)pyridine-2,4-dicarboxamide

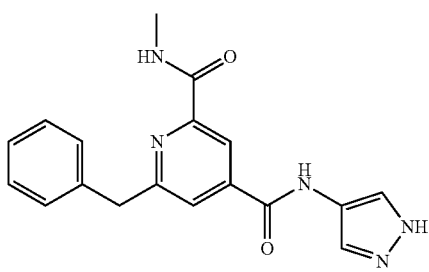 [SMILES: CNC(=O)c1cc(C(=O)Nc2cn[nH]c2)cc(Cc2ccccc2)n1]

To a mixture of 2-benzyl-6-(methylcarbamoyl)isonicotinic acid (251.8 mg, 0.93 mmol) and HATU (565.5 mg, 1.49 mmol) was added 1H-pyrazol-4-amine hydrochloride (166.0 mg, 1.39 mmol) and DMF (4 mL). DIPEA (0.570 mL, 3.26 mmol) was added and the mixture was stirred at rt for 3.5 h. The mixture was concentrated under a stream of nitrogen and then diluted with acetonitrile to a total volume of 5 mL and directly purified by MDAP (5×1 mL injection; high pH) and the required fractions (fraction 1 from each run) were evaporated under a stream of nitrogen. The residues were each redissolved in methanol (~5 mL), combined into a tarred vial and the solvent evaporated under a stream of nitrogen to give a pale yellow solid—6-benzyl-N²-methyl-N⁴-(1H-pyrazol-4-yl)pyridine-2,4-dicarboxamide (198.9 mg, 0.59 mmol, 64% yield)

LCMS (2 min High pH): Rt=0.85 min, [MH]+=336.1.

¹H NMR (400 MHz, DMSO-d6) δ ppm 12.71 (br. s., 1H), 10.88 (s, 1H), 8.78 (q, J=4.5 Hz, 1H), 8.40 (d, J=1.5 Hz, 1H), 8.02 (br. s., 1H), 7.90 (d, J=1.5 Hz, 1H), 7.70 (br. s., 1H), 7.36-7.41 (m, 2H), 7.29-7.36 (m, 2H), 7.19-7.26 (m, 1H), 4.25 (s, 2H), 2.88 (d, J=4.9 Hz, 3H)

Example 80: 6-Benzyl-N⁴-(1-(2-hydroxy-2-methylpropyl)-1H-pyrazol-4-yl)-N²-methylpyridine-2,4-dicarboxamide

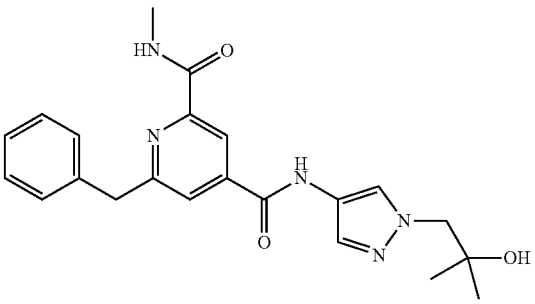 [SMILES: CNC(=O)c1cc(C(=O)Nc2cnn(CC(C)(C)O)c2)cc(Cc2ccccc2)n1]

To a sealed microwave vial containing sodium hydride (60% dispersion in mineral oils, 14.9 mg, 0.37 mmol) and 6-benzyl-N²-methyl-N⁴-(1H-pyrazol-4-yl)pyridine-2,4-dicarboxamide (58.9 mg, 0.18 mmol) was added DMF (1 mL). The mixture was stirred under an atmosphere of nitrogen at rt for 30 min before 2,2-dimethyloxirane (0.019 mL, 0.21 mmol) was added and the mixture stirred at rt for 35 min. The microwave cap was replaced with a new one and the mixture heated in a microwave reactor at 60° C. for 30 min. The microwave cap was replaced with a new one and the mixture heated in a microwave reactor at 80° C. for 30 min. Methanol (0.5 mL) was added to quench the reaction and the resulting orange solution was directly purified by MDAP (2×1 mL injection, formic). The required fractions (fraction 1 from both runs) were evaporated under a stream of nitrogen, the residues were dissolved in dichloromethane (~10 mL), combined and transferred to a tarred vial before the solvent was evaporated under a stream of nitrogen and dried in vacuo to give the desired product as a colourless glass, 6-benzyl-N⁴-(1-(2-hydroxy-2-methylpropyl)-1H-pyrazol-4-yl)-N²-methylpyridine-2,4-dicarboxamide (14.0 mg, 0.03 mmol, 20% yield)

LCMS (2 min High pH): Rt=0.89 min, [MH]+=408.6.

Example 16: (S)-N²-Methyl-6-(1-phenylethyl)-N⁴-(1H-pyrazol-4-yl)pyridine-2,4-dicarboxamide

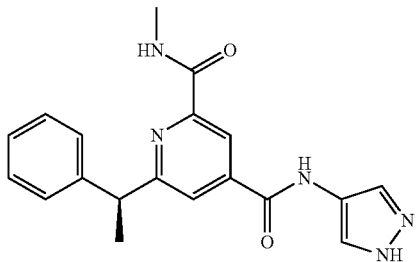 [SMILES: CNC(=O)c1cc(C(=O)Nc2cn[nH]c2)cc([C@@H](C)c2ccccc2)n1]

To a mixture of (S)-2-(methylcarbamoyl)-6-(1-phenylethyl)isonicotinic acid (80.5 mg, 0.28 mmol) and HATU (172.0 mg, 0.45 mmol) was added 1H-pyrazol-4-amine hydrochloride (51.6 mg, 0.43 mmol) and DMF (1.8 mL). DIPEA (0.173 mL, 0.99 mmol) was added and the mixture was stirred at rt for 2 h. The mixture was concentrated under a stream of nitrogen and diluted with acetonitrile to a total volume of 2 mL and directly purified by MDAP (2×1 mL injection; formic) and the required fractions (fraction 1 from both runs) were combined and evaporated in vacuo. The residue was redissolved in methanol (~6 mL) and transferred to a tarred vial, the solvent evaporated under a stream of nitrogen and the residue dried in vacuo to give the desired product as a yellow solid, (S)-N²-methyl-6-(1-phenylethyl)-N⁴-(1H-pyrazol-4-yl)pyridine-2,4-dicarboxamide (87.5 mg, 0.25 mmol, 88% yield)

LCMS (2 min Formic): Rt=0.91 min, [MH]+=350.3.

$^1$H NMR (400 MHz, DMSO-d6) δ ppm 10.87 (s, 1H) 8.80 (d, J=4.2 Hz, 1H), 8.38 (s, 1H) 7.80-7.96 (m, 3H), 7.43 (d, J=7.6 Hz, 2H), 7.31 (t, J=7.2 Hz, 2H), 7.13-7.25 (m, 1H), 4.45 (q, J=6.6 Hz, 2H), 2.91 (d, J=3.9 Hz, 3H), 1.74 (d, J=6.8 Hz, 3H)

The following examples were prepared in a similar manner to example 16 from intermediate 12, (S)-2-(methylcarbamoyl)-6-(1-phenylethyl)isonicotinic acid and the appropriate commercially available amine monomer, to provide the listed examples.

EXAMPLES

| Ex No. | Name | Structure | Mass (mg) | Yield (%) | [MH]+ | Rt (min) |
|---|---|---|---|---|---|---|
| 14 | (S)-N²-Methyl-N⁴-(1-methyl-1H-pyrazol-4-yl)-6-(1-phenylethyl)pyridine-2,4-dicarboxamide | 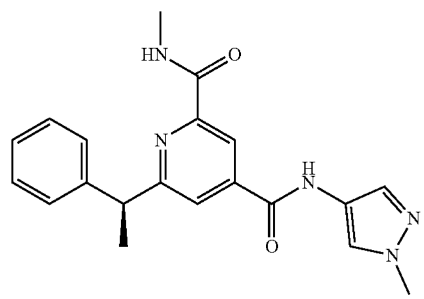 [SMILES: CNC(=O)c1cc(C(=O)Nc2cnn(C)c2)cc([C@@H](C)c2ccccc2)n1] | 55.4 | 92 | 364.4 | 0.98 (high pH) |
| 15 | (S)-N²-Methyl-6-(1-phenylethyl)-N⁴-(1H-pyrazol-3-yl)pyridine-2,4-dicarboxamide | 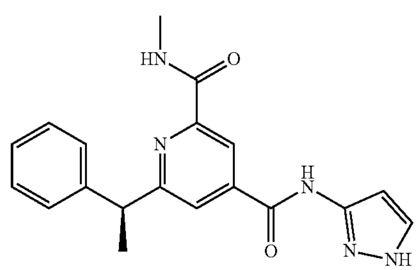 [SMILES: CNC(=O)c1cc(C(=O)Nc2cc[nH]n2)cc([C@@H](C)c2ccccc2)n1] | 14.9 | 27 | 350.3 | 0.95 (High pH) |
| 17 | (S)-N²-Methyl-6-(1-phenylethyl)-N⁴-(2-(pyridin-2-yl)ethyl)pyridine-2,4-dicarboxamide | 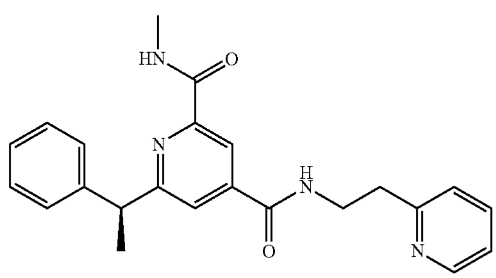 [SMILES: CNC(=O)c1cc(C(=O)NCCc2ccccn2)cc([C@@H](C)c2ccccc2)n1] | 63.7 | 89 | 389.4 | 1.01 (High pH) |

-continued

| Ex No. | Name | Structure | Mass (mg) | Yield (%) | [MH]+ | Rt (min) |
|---|---|---|---|---|---|---|
| 18 | (S)-N²-Methyl-6-(1-phenylethyl)-N⁴-(2-(pyridin-3-yl)ethyl)pyridine-2,4-dicarboxamide | 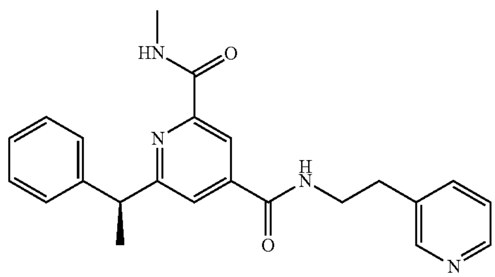 [SMILES: CNC(=O)c1cc(C(=O)NCCc2cccnc2)cc([C@@H](C)c2ccccc2)n1] | 56.9 | 82 | 389.4 | 0.98 (High pH) |
| 19 | (S)-N⁴-(2-(1H-Pyrazol-4-yl)ethyl)-N²-methyl-6-(1-phenyl-ethyl)pyridine-2,4-dicarboxamide | 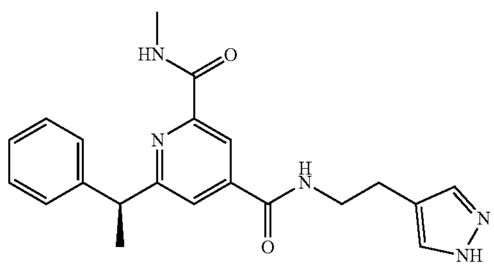 [SMILES: CNC(=O)c1cc(C(=O)NCCc2cn[nH]c2)cc([C@@H](C)c2ccccc2)n1] | 45.4 | 68 | 378.4 | 0.92 (High pH) |
| 22 | (S)-N²-Methyl-N⁴-(2-(1-methyl-1H-pyrazol-3-yl)ethyl)-6-(1-phenyl-ethyl)pyridine-2,4-dicarboxamide | 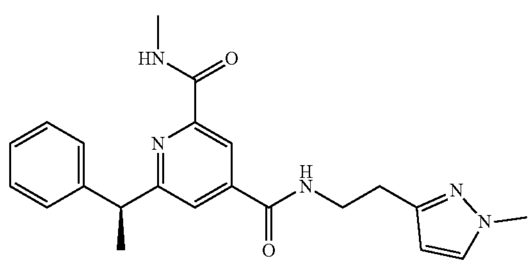 [SMILES: CNC(=O)c1cc(C(=O)NCCc2ccn(C)n2)cc([C@@H](C)c2ccccc2)n1] | 52.8 | 78 | 392.4 | 0.96 (High pH) |
| 23 | (S)-N⁴-(2-(1H-Pyrazol-5-yl)ethyl)-N²-methyl-6-(1-phenyl-ethyl)pyridine-2,4-dicarboxamide | 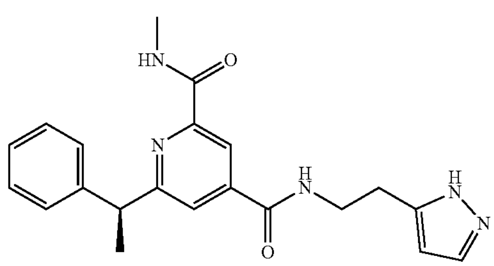 [SMILES: CNC(=O)c1cc(C(=O)NCCc2ccn[nH]2)cc([C@@H](C)c2ccccc2)n1] | 47 | 70 | 378.4 | 0.93 (High pH) |
| 25 | (S)-N²-Methyl-N⁴-(1-methyl-1H-pyrazol-3-yl)-6-(1-phenyl-ethyl)pyridine-2,4-dicarboxamide | 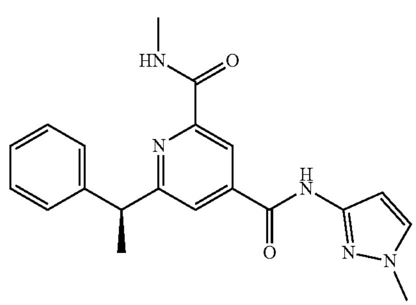 [SMILES: CNC(=O)c1cc(C(=O)Nc2ccn(C)n2)cc([C@@H](C)c2ccccc2)n1] | 61.5 | 98 | 364.3 | 0.98 (formic) |

| Ex No. | Name | Structure | Mass (mg) | Yield (%) | [MH]+ | Rt (min) |
|---|---|---|---|---|---|---|
| 26 | (S)-N⁴-(2-(1H-1,2,3-Triazol-1-yl)ethyl)-N²-methyl-6-(1-phenyl-ethyl)pyridine-2,4-dicarboxamide | 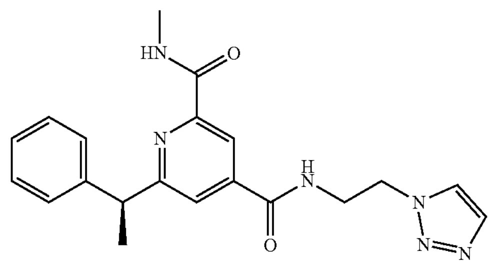 [SMILES: CNC(=O)c1cc(C(=O)NCCn2ccnn2)cc([C@@H](C)c2ccccc2)n1] | 54.9 | 100 | 379.4 | 0.89 (High pH) |
| 27 | (S)-N⁴-(2-(1H-Pyrazol-1-yl)ethyl)-N²-methyl-6-(1-phenyl-ethyl)pyridine-2,4-dicarboxamide | 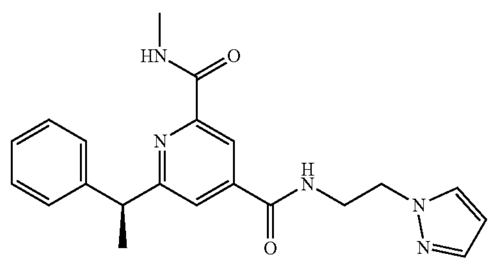 [SMILES: CNC(=O)c1cc(C(=O)NCCn2cccn2)cc([C@@H](C)c2ccccc2)n1] | 50.8 | 89 | 378.4 | 0.96 (High pH) |
| 29 | (S)-N⁴-(2-(Isoxazol-4-yl)ethyl)-N²-methyl-6-(1-phenyl-ethyl)pyridine-2,4-dicarboxamide | 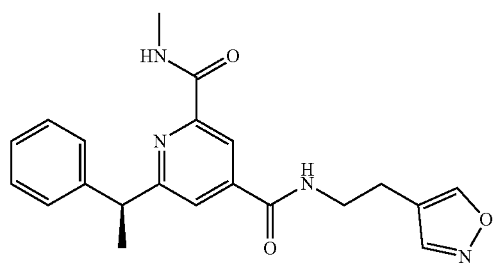 [SMILES: CNC(=O)c1cc(C(=O)NCCc2cnoc2)cc([C@@H](C)c2ccccc2)n1] | 47.9 | 87 | 379.4 | 1.00 (High pH) |
| 31 | (S)-N²-Methyl-6-(1-phenylethyl)-N⁴-(pyridazin-4-yl)pyridine-2,4-dicarboxamide | 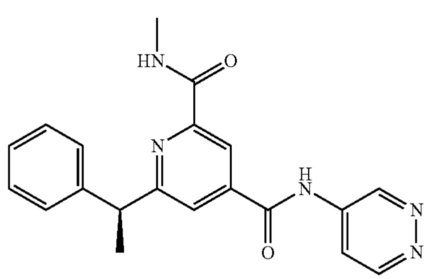 [SMILES: CNC(=O)c1cc(C(=O)Nc2ccnnc2)cc([C@@H](C)c2ccccc2)n1] | 22.3 | 49 | 362.3 | 0.90 (formic) |
| 32 | (S)-N²-Methyl-N⁴-(1-methyl-1H-1,2,4-triazol-3-yl)-6-(1-phenyl-ethyl)pyridine-2,4-dicarboxamide | 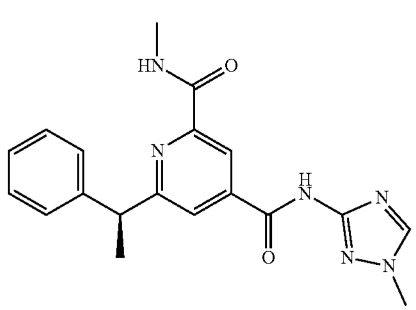 [SMILES: CNC(=O)c1cc(C(=O)Nc2ncn(C)n2)cc([C@@H](C)c2ccccc2)n1] | 14.7 | 28 | 365.3 | 0.84 (formic) |

-continued

| Ex No. | Name | Structure | Mass (mg) | Yield (%) | [MH]+ | Rt (min) |
|---|---|---|---|---|---|---|
| 33 | (S)-N²-Methyl-N⁴-(2-(4-methylthiazol-5-yl)ethyl)-6-(1-phenyl-ethyl)pyridine-2,4-dicarboxamide | 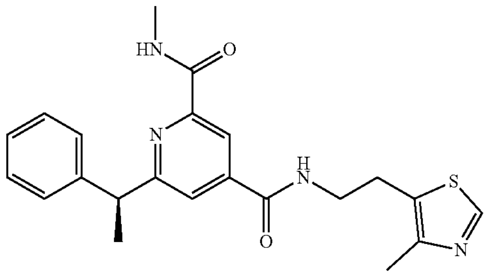 [SMILES: CNC(=O)c1cc(C(=O)NCCc2scnc2C)cc([C@@H](C)c2ccccc2)n1] | 30 | 52 | 409.4 | 1.01 (formic) |
| 35 | (S)-N²-Methyl-6-(1-phenylethyl)-N⁴-(2-(thiazol-4-yl)ethyl)pyridine-2,4-dicarboxamide | 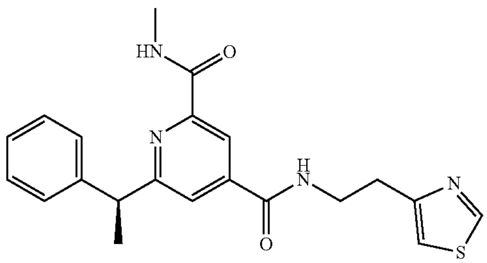 [SMILES: CNC(=O)c1cc(C(=O)NCCc2cscn2)cc([C@@H](C)c2ccccc2)n1] | 25 | 52 | 395.3 | 0.98 (formic) |
| 39 | (S)-N²-Methyl-N⁴-(2-(4-methyl-4H-1,2,4-triazol-3-yl)ethyl)-6-(1-phenyl-ethyl)pyridine-2,4-dicarboxamide | 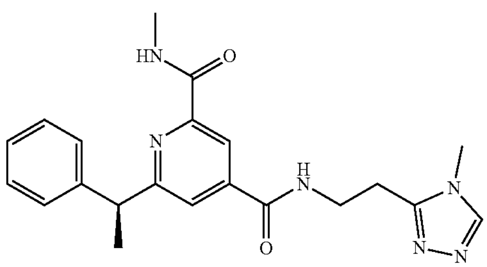 [SMILES: CNC(=O)c1cc(C(=O)NCCc2nncn2C)cc([C@@H](C)c2ccccc2)n1] | 96.5 | 99 | 393.4 | 0.74 (formic) |
| 40 | (S)-N²-Methyl-N⁴-(2-(5-methyl-1,3,4-oxadiazol-2-yl)ethyl)-6-(1-phenyl-ethyl)pyridine-2,4-dicarboxamide | 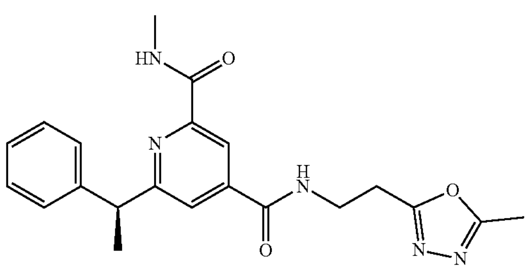 [SMILES: CNC(=O)c1cc(C(=O)NCCc2nnc(C)o2)cc([C@@H](C)c2ccccc2)n1] | 35 | 63 | 394.4 | 1.00 (High pH) |
| 41 | (S)-N²-Methyl-N⁴-((1-methyl-1H-pyrazol-3-yl)methyl)-6-(1-phenyl-ethyl)pyridine-2,4-dicarboxamide | 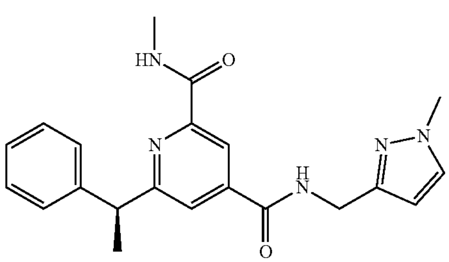 [SMILES: CNC(=O)c1cc(C(=O)NCc2ccn(C)n2)cc([C@@H](C)c2ccccc2)n1] | 32 | 60 | 378.4 | 0.96 (High pH) |

-continued

| Ex No. | Name | Structure | Mass (mg) | Yield (%) | [MH]+ | Rt (min) |
|---|---|---|---|---|---|---|
| 42 | (S)-N4-(1-(2-Hydroxyethyl)-1H-pyrazol-4-yl)-N2-methyl-6-(1-phenylethyl)pyridine-2,4-dicarboxamide | 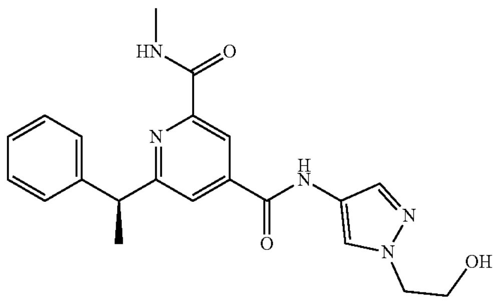 [SMILES: CNC(=O)c1cc(C(=O)Nc2cnn(CCO)c2)cc([C@@H](C)c2ccccc2)n1] | 26.8 | 40 | 394.4 | 0.88 (formic) |
| 43 | (S)-N2-Methyl-6-(1-phenylethyl)-N4-(pyrimidin-5-yl)pyridine-2,4-dicarboxamide | 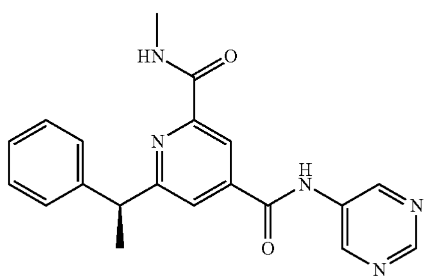 [SMILES: CNC(=O)c1cc(C(=O)Nc2cncnc2)cc([C@@H](C)c2ccccc2)n1] | 23.8 | 45 | 362.3 | 0.97 (High pH) |
| 44 | (S)-N2-Methyl-N4-(2-methyl-2H-tetrazol-5-yl)-6-(1-phenylethyl)pyridine-2,4-dicarboxamide | 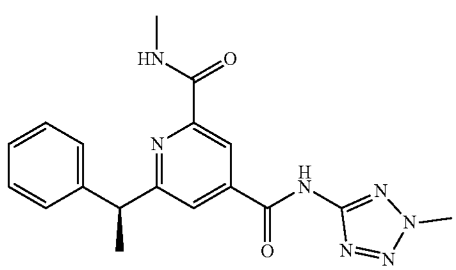 [SMILES: CNC(=O)c1cc(C(=O)Nc2nnn(C)n2)cc([C@@H](C)c2ccccc2)n1] | 15 | 29 | 366.3 | 0.85 (High pH) |
| 47 | (S)-N2-Methyl-N4-(2-(1-methyl-1H-1,2,4-triazol-5-yl)ethyl)-6-(1-phenylethyl)pyridine-2,4-dicarboxamide | 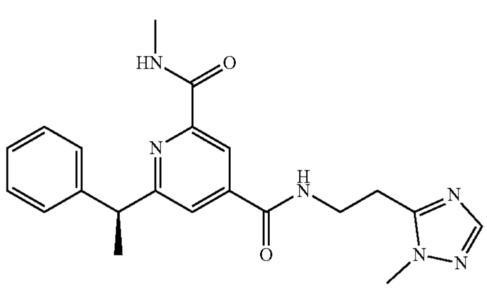 [SMILES: CNC(=O)c1cc(C(=O)NCCc2ncnn2C)cc([C@@H](C)c2ccccc2)n1] | 49.9 | 85 | 393.4 | 0.89 (High pH) |

-continued

| Ex No. | Name | Structure | Mass (mg) | Yield (%) | [MH]+ | Rt (min) |
|---|---|---|---|---|---|---|
| 50 | (S)-N⁴-(1-(2-Hydroxyethyl)-1H-pyrazol-3-yl)-N²-methyl-6-(1-phenylethyl)pyridine-2,4-dicarboxamide | 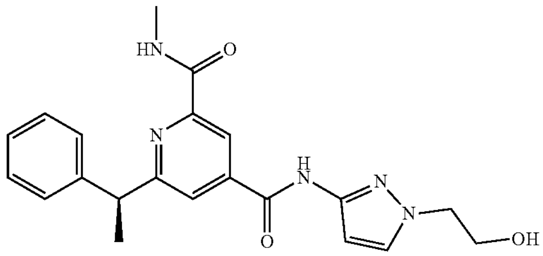 [SMILES: CNC(=O)c1cc(C(=O)Nc2ccn(CCO)n2)cc([C@@H](C)c2ccccc2)n1] | 48.4 | 70 | 394.4 | 0.91 (High pH) |
| 78 | (S)-N²-Methyl-6-(1-phenylethyl)pyridine-2,4-dicarboxamide | 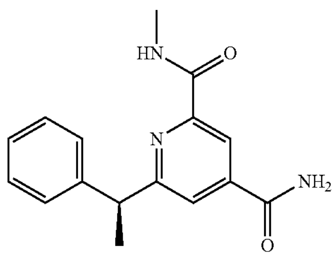 [SMILES: CNC(=O)c1cc(C(N)=O)cc([C@@H](C)c2ccccc2)n1] | 58 | 58 | 284.3 | 0.88 (High pH) |

Example 21: (R)-N²-Methyl-6-(1-phenylethyl)-N⁴-(1H-pyrazol-4-yl)pyridine-2,4-dicarboxamide

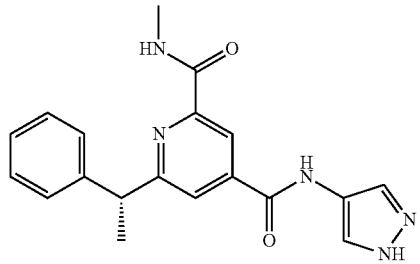 [SMILES: CNC(=O)c1cc(C(=O)Nc2cn[nH]c2)cc([C@H](C)c2ccccc2)n1]

To a mixture of (R)-2-(methylcarbamoyl)-6-(1-phenylethyl)isonicotinic acid (53.7 mg, 0.19 mmol), HATU (86.7 mg, 0.23 mmol) and 1H-pyrazol-4-amine, hydrochloride (28.9 mg, 0.24 mmol) in DMF (1 mL) was added DIPEA (0.132 mL, 0.76 mmol). The resulting dark grey solution was stirred at rt for 2.75 h. The reaction mixture was diluted with DMSO (2 mL) and directly purified by MDAP (3 mL injection, high pH). The required fractions (fractions 1 and 2) were combined and evaporated in vacuo to give the desired product as a light yellow solid—(R)-N²-methyl-6-(1-phenylethyl)-N⁴-(1H-pyrazol-4-yl)pyridine-2,4-dicarboxamide (39.9 mg, 0.11 mmol, 61% yield)

LCMS (2 min High pH): Rt=0.92 min, [MH]+=350.3.

Example 36: 6-((1H-Indol-4-yl)methyl)-N²-methyl-N⁴-(2-(1-methyl-1H-pyrazol-4-yl)ethyl)pyridine-2,4-dicarboxamide

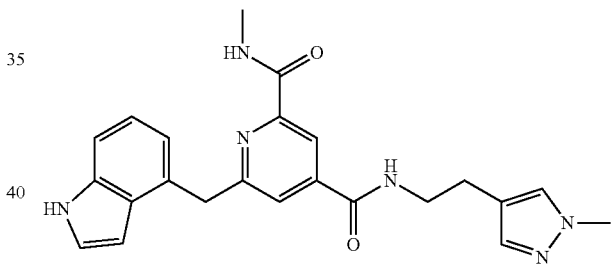

To a mixture of 2-((1H-indol-4-yl)methyl)-6-(methylcarbamoyl)isonicotinic acid (30.1 mg, 0.10 mmol) and HATU (58.5 mg, 0.15 mmol) was added a solution of 2-(1-methyl-1H-pyrazol-4-yl)ethanamine (21.9 mg, 0.18 mmol) in DMF (0.8 mL) followed by DIPEA (0.050 mL, 0.29 mmol) and the mixture was stirred at rt for 20 min before being left to stand for 15 h. The mixture was then concentrated under a stream of nitrogen and diluted with acetonitrile to a total volume of 1 mL and directly purified by MDAP (1×1 mL injection; formic) and the required fraction (fraction 1) was evaporated under a stream of nitrogen. The residue was redissolved in dichloromethane (~6 mL) and methanol (~3 mL) and was transferred to a tarred vial, the solvent evaporated under a stream of nitrogen and the residue dried in vacuo to give the desired product as a light brown solid—6-((1H-indol-4-yl)methyl)-N²-methyl-N⁴-(2-(1-methyl-1H-pyrazol-4-yl)ethyl)pyridine-2,4-dicarboxamide (25.8 mg, 0.06 mmol, 64% yield)

LCMS (2 min Formic): Rt=0.82 min, [MH]+=417.4.

The following examples were prepared in a similar manner to example 36 from intermediate 15, 2-((1H-indol-4-yl)methyl)-6-(methylcarbamoyl)isonicotinic acid and the appropriate commercially available amine monomer, to provide the listed examples.

EXAMPLES

| Ex No. | Name | Structure | Mass (mg) | Yield (%) | [MH]+ | Rt (min) |
|---|---|---|---|---|---|---|
| 37 | 6-((1H-Indol-4-yl)methyl)-$N^4$-(2-(1H-pyrazol-3-yl)ethyl)-$N^2$-methylpyridine-2,4-dicarboxamide | 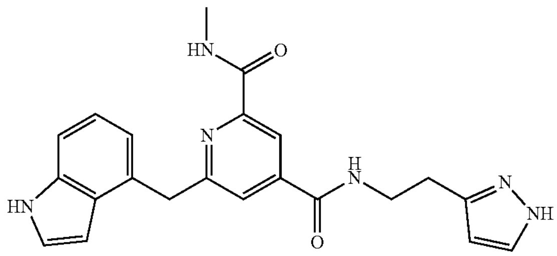 [SMILES: CNC(=O)c1cc(C(=O)NCCc2cc[nH]n2)cc(Cc2cccc3[nH]ccc23)n1] | 21.4 | 56 | 403.4 | 0.78 (formic) |
| 38 | 6-((1H-Indol-4-yl)methyl)-$N^2$-methyl-$N^4$-(1-methyl-1H-pyrazol-4-yl)pyridine-2,4-dicarboxamide | 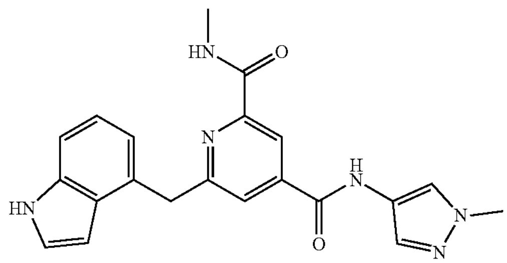 [SMILES: CNC(=O)c1cc(C(=O)Nc2cnn(C)c2)cc(Cc2cccc3[nH]ccc23)n1] | 15.5 | 41 | 389.4 | 0.84 (formic) |
| 48 | 6-((1H-Indol-4-yl)methyl)-$N^2$-methyl-$N^4$-(1H-pyrazol-4-yl)pyridine-2,4-dicarboxamide | 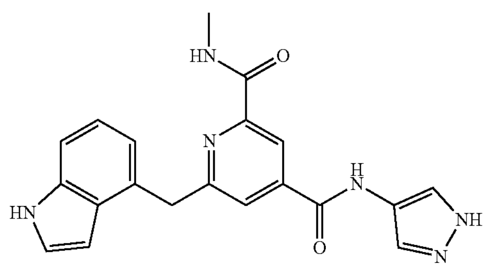 [SMILES: CNC(=O)c1cc(C(=O)Nc2cn[nH]c2)cc(Cc2cccc3[nH]ccc23)n1] | 34.9 | 76 | 375.4 | 0.81 (High pH) |
| 79 | 6-((1H-Indol-4-yl)methyl)-$N^2$-methylpyridine-2,4-dicarboxamide | 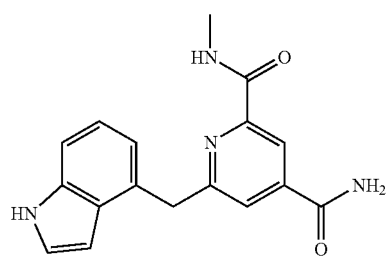 [SMILES: CNC(=O)c1cc(C(N)=O)cc(Cc2cccc3[nH]ccc23)n1] | 15 | 39 | 309.2 | 0.75 (Formic) |

Example 45: (+/−)-6-(Hydroxy(phenyl)methyl)-$N^2$-methyl-$N^4$-(1-methyl-1H-pyrazol-4-yl)pyridine-2,4-dicarboxamide

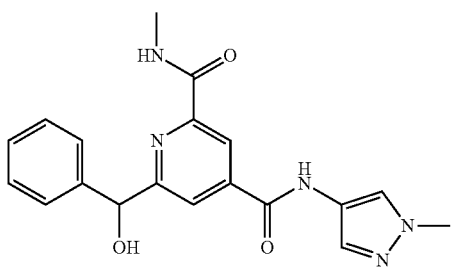 [SMILES: CNC(=O)c1cc(C(=O)Nc2cnn(C)c2)cc(C(O)c2ccccc2)n1]

To a solution of (±)-2-(hydroxy(phenyl)methyl)-6-(methylcarbamoyl)isonicotinic acid (48.1 mg, 0.17 mmol), HATU (94.4 mg, 0.25 mmol) and 1-methyl-1H-pyrazol-4-amine, hydrochloride (35.5 mg, 0.27 mmol) in DMF (1.0 mL) was added DIPEA (0.117 mL, 0.67 mmol). The resulting dark orange solution was stirred at rt for 2 h, after which it was diluted with DMSO (2 mL) and directly purified by MDAP (3 mL injection, high pH). The required fractions (fractions 1 and 2) were evaporated under a stream of nitrogen, redissolved in methanol (2 mL each) and dichloromethane (1 mL each) and combined. This solution was evaporated under a stream of nitrogen and the residue dried in vacuo to give the desired product as a light green solid—(±)-6-(hydroxy(phenyl)methyl)-$N^2$-methyl-$N^4$-(1-methyl-1H-pyrazol-4-yl)pyridine-2,4-dicarboxamide (52.4 mg, 0.14 mmol, 85% yield).

LCMS (2 min High pH): Rt=0.77 min, [MH]+=366.3.

The following examples were prepared in a similar manner to example 45 from intermediate 17, (±)-2-(hydroxy(phenyl)methyl)-6-(methylcarbamoyl)isonicotinic acid and the appropriate commercially available amine monomer, to provide the listed examples.

Examples

| Ex No. | Name | Structure | Mass (mg) | Yield (%) | [MH]+ | Rt (min) |
|---|---|---|---|---|---|---|
| 46 | (+/−)-6-(Hydroxy (phenyl)methyl)-N²-methyl-N⁴-(2-(1-methyl-1H-pyrazol-4-yl)ethyl)pyridine-2,4-dicarboxamide | 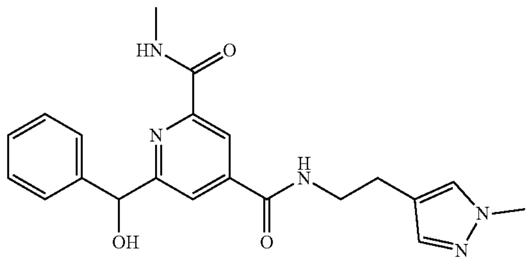 [SMILES: CNC(=O)c1cc(C(=O)NCCc2cnn(C)c2)cc(C(O)c2ccccc2)n1] | 58.2 | 88 | 394.4 | 0.77 (High pH) |

Example 49: (S*)-6-(Hydroxy(phenyl)methyl)-N²-methyl-N⁴-(2-(1-methyl-1H-pyrazol-4-yl)ethyl)pyridine-2,4-dicarboxamide Example 77: (R*)-6-(Hydroxy(phenyl)methyl)-N²-methyl-N⁴-(2-(1-methyl-1H-pyrazol-4-yl)ethyl)pyridine-2,4-dicarboxamide

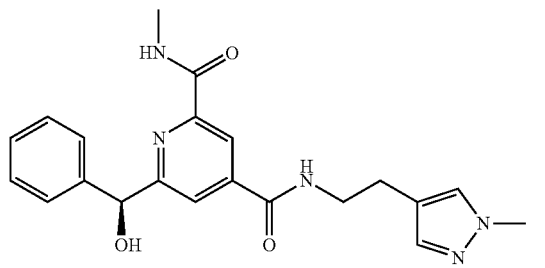

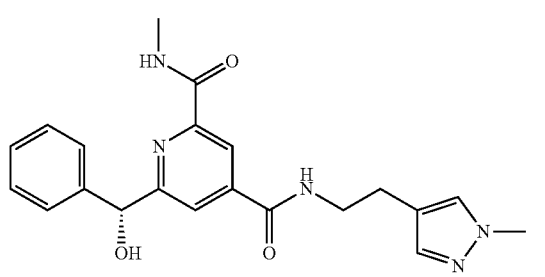

(+/−)-6-(Hydroxy(phenyl)methyl)-N²-methyl-N⁴-(2-(1-methyl-1H-pyrazol-4-yl)ethyl)pyridine-2,4-dicarboxamide (for a preparation see Example 46) (52 mg) was purified by chiral HPLC. The racemate was dissolved in EtOH (2 mL). Injection: 1 mL of the solution was injected onto the column (30% EtOH/heptane, flow rate=30 mL/min, detection wavelength=215 nm, 4. Ref 550, 100, Column 30 mm×25 cm Chiralpak IA (5 μm), lot no. IA11321-01). Total number of injections=7. Fractions from 24-29 min were bulked and labelled peak 1. Fractions from 29-37 min were bulked and labelled mix, Fractions from 37-50 min were bulked and labelled peak 2. The bulked mixed fractions were concentrated in vacuo and reprocessed using the above method. The bulked pure fractions were concentrated in vacuo and then transferred to weighed flasks.

The fractions corresponding to peak 1 were collected to afford example 77 (25 mg)

LCMS (2 min High pH): Rt=0.76 min, [MH]+=394.4.

The fractions corresponding to peak 2 were collected to afford example 49 (21 mg)

LCMS (2 min High pH): Rt=0.76 min, [MH]+=394.4.

Example 52: (S*)-6-(Hydroxy(phenyl)methyl)-N²-methyl-N⁴-(1-methyl-1H-pyrazol-4-yl)pyridine-2,4-dicarboxamide Example 53: (R*)-6-(Hydroxy(phenyl)methyl)-N²-methyl-N⁴-(1-methyl-1H-pyrazol-4-yl)pyridine-2,4-dicarboxamide

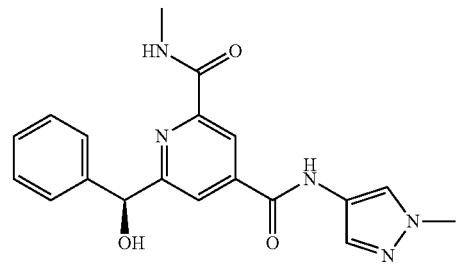

-continued

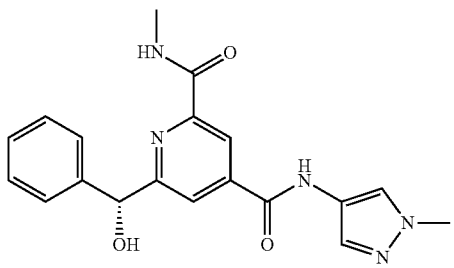

Example 45 (45 mg) was purified by chiral HPLC. The racemate was dissolved in EtOH (3 mL) with heating. Injection: 1.5 mL of the solution was injected onto the column (20% EtOH/heptane, flow rate=20 mL/min, detection wavelength=215 nm, 4. Ref 550, 100, Column 21.1 mm×25 cm (R-R) Whelk O-1 (5 µm), lot no. #49788). Total number of injections=3. Fractions from 23.5-26 min were bulked and labelled peak 1. Fractions from 26-28 min were bulked and labelled mix, Fractions from 28-32 min were bulked and labelled peak 2. The bulked mixed fractions were concentrated in vacuo and reprocessed using the above method. The bulked pure fractions were concentrated in vacuo and then transferred to weighed flasks.

The fractions corresponding to peak 1 were collected to afford example 52 (20 mg)

LCMS (2 min Formic): Rt=0.75 min, [MH]+=366.3.

The fractions corresponding to peak 2 were collected to afford example 53 (20 mg)

LCMS (2 min Formic): Rt=0.73 min, [MH]+=366.3.

Example 54: (+/−)-6-(Methoxy(phenyl)methyl)-$N^2$-methyl-$N^4$-(1H-pyrazol-4-yl)pyridine-2,4-dicarboxamide

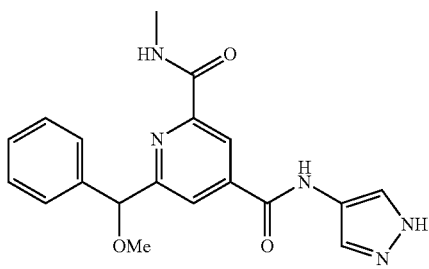 [SMILES: CNC(=O)c1cc(C(=O)Nc2cn[nH]c2)cc(C(OC)c2ccccc2)n1]

2-(Methoxy(phenyl)methyl)-6-(methylcarbamoyl)isonicotinic acid (150 mg, 0.50 mmol) was added to a dry flask. DMF (2 mL) was added, followed by HATU (228 mg, 0.60 mmol) and 1H-pyrazol-4-amine, hydrochloride (59.7 mg, 0.50 mmol). The reaction was stirred for 2 min and then DIPEA (0.262 mL, 1.498 mmol) was added. The reaction was stirred at rt for 30 min. The reaction mixture was added directly to 3× LCMS vials, diluting with DMSO/MeOH and purified by 3× MDAP (High pH). The appropriate fractions were concentrated in vacuo to afford the desired product as a yellow solid—(+/−)-6-(methoxy(phenyl)methyl)-$N^2$-methyl-$N^4$-(1H-pyrazol-4-yl)pyridine-2,4-dicarboxamide (100 mg, 0.27 mmol, 55% yield)

LCMS (2 min Formic): Rt=0.82 min, [MH]+=366.3.

$^1$H NMR (400 MHz, DMSO-d6) δ ppm 12.69 (br. s., 1H) 10.92 (s, 1H), 8.67 (q, J=4.8 Hz, 1H), 8.45 (d, J=1.7 Hz, 1H), 8.17 (d, J=1.5 Hz, 1H), 8.04 (br. s., 1H), 7.72 (br. s., 1H), 7.51 (d, J=7.1 Hz, 2H), 7.36 (t, J=7.5 Hz, 2H), 7.24-7.31 (m, 1H), 5.52 (s, 1H), 3.39 (s, 3H), 2.88 (d, J=4.9 Hz, 3H)

Example 55: (S*)-6-(Methoxy(phenyl)methyl)-$N^2$-methyl-$N^4$-(1H-pyrazol-4-yl)pyridine-2,4-dicarboxamide Example 56: (R*)-6-(Methoxy(phenyl)methyl)-$N^2$-methyl-$N^4$-(1H-pyrazol-4-yl)pyridine-2,4-dicarboxamide

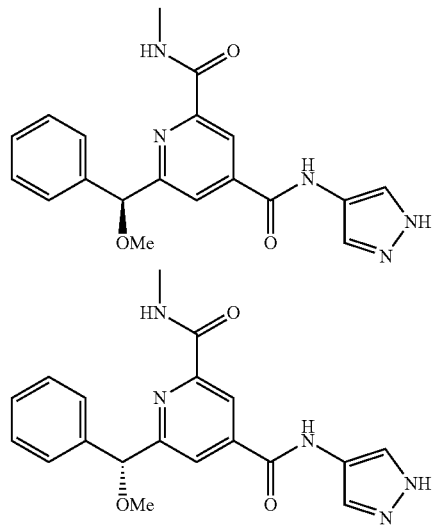

(+/−)-6-(Methoxy(phenyl)methyl)-$N^2$-methyl-$N^4$-(1H-pyrazol-4-yl)pyridine-2,4-dicarboxamide (for a preparation see Example 54) (90 mg) was purified by chiral HPLC. The racemate was dissolved in EtOH (2 mL). Injection: 1.5 mL of the solution was injected onto the column (20% EtOH (+0.2% isopropylamine)/heptane (+0.2% isopropylamine), flow rate=30 mL/min, detection wavelength=215 nm, 4. Ref 550, 100, Column 30 mm×25 cm Chiralcel OD-H (5 µm), lot no. ODH11158-01). Total number of injections=1. Fractions from 9-11 min were bulked and labelled peak 1. Fractions from 12.5-17 min were bulked and labelled peak 2. The bulked pure fractions were concentrated in vacuo and then transferred to weighed flasks.

The fractions corresponding to peak 1 were collected to afford example 55 (35.4 mg)

LCMS (2 min Formic): Rt=0.83 min, [MH]+=366.2.

1H NMR (400 MHz, DMSO-d6) δ ppm 12.69 (br. s., 1H), 10.93 (s, 1H) 8.67 (q, J=4.3 Hz, 1H), 8.45 (d, J=1.7 Hz, 1H), 8.17 (d, J=1.7 Hz, 1H), 8.04 (br. s., 1H), 7.72 (br. s., 1H), 7.51 (d, J=7.1 Hz, 2H), 7.33-7.39 (m, 2H), 7.24-7.30 (m, 1H), 5.52 (s, 1H), 3.39 (s, 3H), 2.88 (d, J=4.9 Hz, 3H)

The fractions corresponding to peak 2 were collected to afford example 56 (39.2 mg)

LCMS (2 min Formic): Rt=0.83 min, [MH]+=366.3.

Examples 57-76 and 81

Examples 57-76 and 81 were prepared in an analogous manner to other examples described above.

| Ex No. | Name | Structure | [MH]$^+$ | Rt (min) |
|---|---|---|---|---|
| 57 | 6-Benzyl-N$^4$-ethyl-N$^2$-methylpyridine-2,4-dicarboxamide | 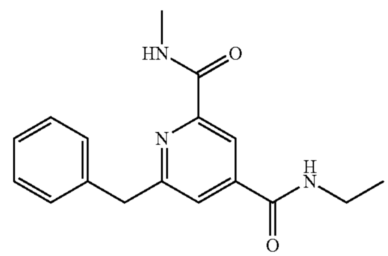 [SMILES: CCNC(=O)c1cc(Cc2ccccc2)nc(C(=O)NC)c1] | 298.3 | 0.91 (formic) |
| 58 | 6-Benzyl-N$^4$-(2-methoxyethyl)-N$^2$-methylpyridine-2,4-dicarboxamide | 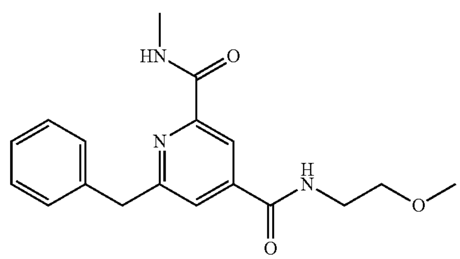 [SMILES: CNC(=O)c1cc(C(=O)NCCOC)cc(Cc2ccccc2)n1] | 328.2 | 0.91 (High pH) |
| 59 | 6-(3-Methoxybenzyl)-N$^4$-(2-methoxyethyl)-N$^2$-methylpyridine-2,4-dicarboxamide | 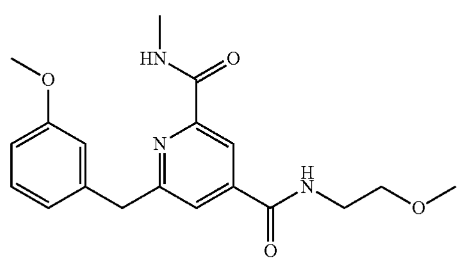 [SMILES: CNC(=O)c1cc(C(=O)NCCOC)cc(Cc2cccc(OC)c2)n1] | 358.3 | 0.91 (High pH) |
| 60 | 6-Benzyl-N$^4$-isopropyl-N$^2$-methylpyridine-2,4-dicarboxamide | 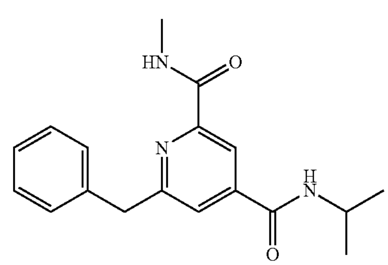 [SMILES: CNC(=O)c1cc(C(=O)NC(C)C)cc(Cc2ccccc2)n1] | 312.2 | 0.97 (High pH) |
| 61 | (+/−)-6-Benzyl-N$^4$-(2-hydroxypropyl)-N$^2$-methylpyridine-2,4-dicarboxamide | 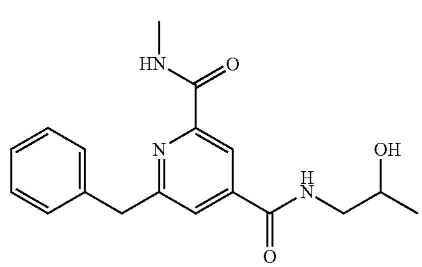 [SMILES: CNC(=O)c1cc(C(=O)NCC(C)O)cc(Cc2ccccc2)n1] | 328.1 | 0.80 (formic) |

| Ex No. | Name | Structure | [MH]⁺ | Rt (min) |
|---|---|---|---|---|
| 62 | 6-Benzyl-$N^4$-(2-hydroxyethyl)-$N^2$-methylpyridine-2,4-dicarboxamide | 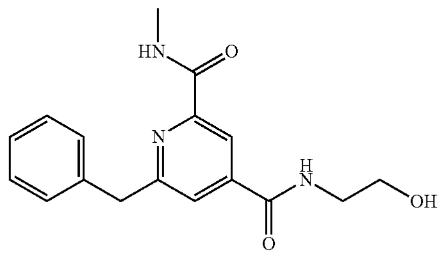 [SMILES: CNC(=O)c1cc(C(=O)NCCO)cc(Cc2ccccc2)n1] | 314.1 | 0.76 (formic) |
| 63 | 6-Benzyl-$N^4$-(3-(dimethylamino)propyl)-$N^2$-methylpyridine-2,4-dicarboxamide | 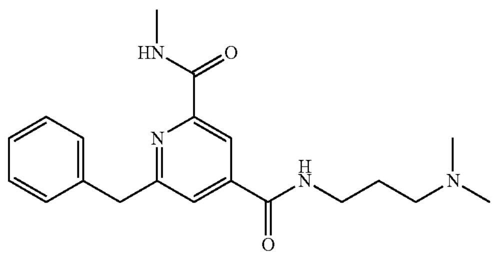 [SMILES: CNC(=O)c1cc(C(=O)NCCCN(C)C)cc(Cc2ccccc2)n1] | 355.3 | 0.59 (formic) |
| 64 | $N^4$-(3-Aminopropyl)-6-benzyl-$N^2$-methylpyridine-2,4-dicarboxamide hydrochloride | 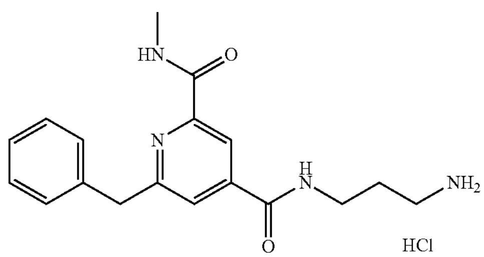 [SMILES: CNC(=O)c1cc(C(=O)NCCCN)cc(Cc2ccccc2)n1 ; Cl] | 327.3 | 0.55 (formic) |
| 65 | 6-Benzyl-$N^4$-isobutyl-$N^2$-methylpyridine-2,4-dicarboxamide | 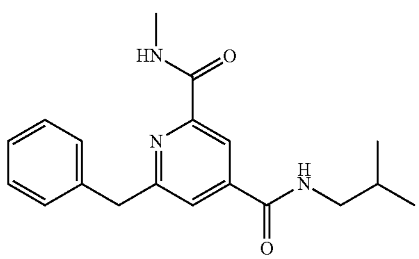 [SMILES: CNC(=O)c1cc(C(=O)NCC(C)C)cc(Cc2ccccc2)n1] | 326.3 | 1.07 (High pH) |
| 66 | 6-Benzyl-$N^4$-(tert-butyl)-$N^2$-methylpyridine-2,4-dicarboxamide | 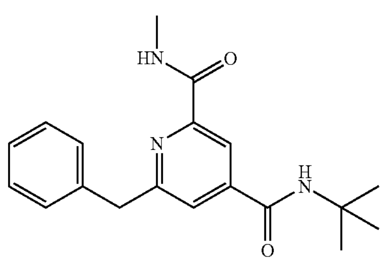 [SMILES: CNC(=O)c1cc(C(=O)NC(C)(C)C)cc(Cc2ccccc2)n1] | 326.3 | 1.10 (High pH) |
| 67 | 6-Benzyl-$N^2$-methyl-$N^4$-(1-methyl-1H-pyrazol-5-yl)pyridine-2,4-dicarboxamide | 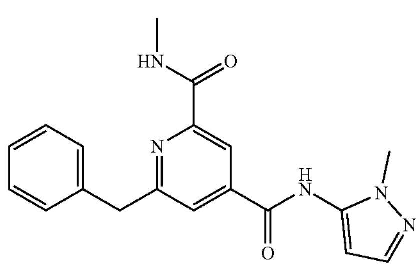 [SMILES: CNC(=O)c1cc(C(=O)Nc2ccnn2C)cc(Cc2ccccc2)n1] | 350.3 | 0.90 (High pH) |

| Ex No. | Name | Structure | [MH]+ | Rt (min) |
|---|---|---|---|---|
| 68 | (S)-N4-(2-(1H-1,2,4-Triazol-1-yl)ethyl)-N2-methyl-6-(1-phenylethyl)pyridine-2,4-dicarboxamide | 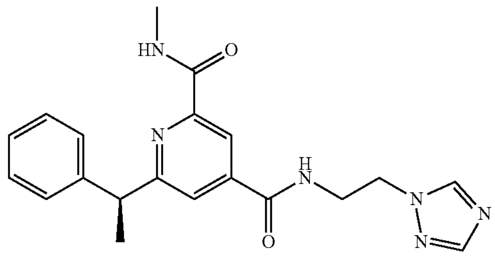 [SMILES: CNC(=O)c1cc(C(=O)NCCn2cncn2)cc([C@@H](C)c2ccccc2)n1] | 379.4 | 0.87 (High pH) |
| 69 | (S)-N4-(2-(1H-Imidazol-1-yl)ethyl)-N2-methyl-6-(1-phenylethyl)pyridine-2,4-dicarboxamide | 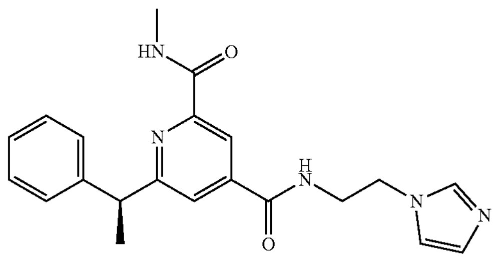 [SMILES: CNC(=O)c1cc(C(=O)NCCn2ccnc2)cc([C@@H](C)c2ccccc2)n1] | 378.4 | 0.90 (High pH) |
| 70 | (S)-N2-Methyl-6-(1-phenylethyl)-N4-(2-(thiazol-2-yl)ethyl)pyridine-2,4-dicarboxamide | 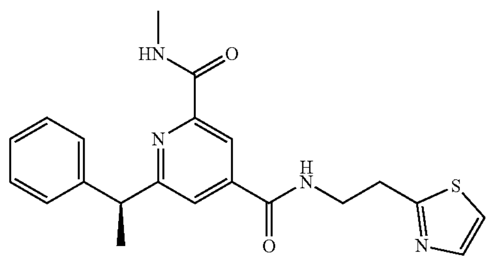 [SMILES: CNC(=O)c1cc(C(=O)NCCc2nccs2)cc([C@@H](C)c2ccccc2)n1] | 395.4 | 1.01 (High pH) |
| 71 | (S)-N2-Methyl-N4-(2-(2-methyl-1H-imidazol-1-yl)ethyl)-6-(1-phenylethyl)pyridine-2,4-dicarboxamide | 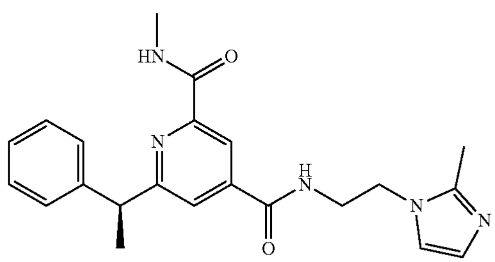 [SMILES: CNC(=O)c1cc(C(=O)NCCn2ccnc2C)cc([C@@H](C)c2ccccc2)n1] | 392.4 | 0.91 (High pH) |
| 72 | (S)-N2-Methyl-N4-(4-methyl-1H-pyrazol-3-yl)-6-(1-phenylethyl)pyridine-2,4-dicarboxamide | 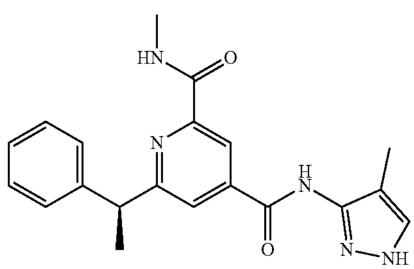 [SMILES: CNC(=O)c1cc(C(=O)Nc2n[nH]cc2C)cc([C@@H](C)c2ccccc2)n1] | 364.3 | 1.03 (formic) |
| 73 | (S)-N2-Methyl-N4-(3-methyl-1H-pyrazol-4-yl)-6-(1-phenylethyl)pyridine-2,4-dicarboxamide | 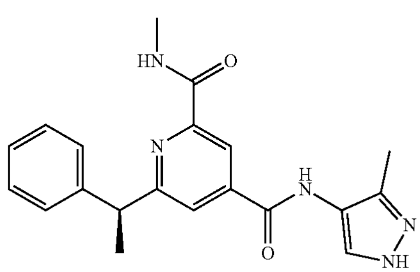 [SMILES: CNC(=O)c1cc(C(=O)Nc2c[nH]nc2C)cc([C@@H](C)c2ccccc2)n1] | 364.4 | 0.93 (High pH) |

| Ex No. | Name | Structure | [MH]⁺ | Rt (min) |
|---|---|---|---|---|
| 74 | (S)-$N^2$-Methyl-$N^4$-(3-methyl-1,2,4-oxadiazol-5-yl)-6-(1-phenylethyl)pyridine-2,4-dicarboxamide | 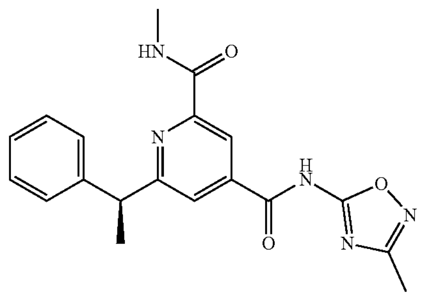 [SMILES: CNC(=O)c1cc(C(=O)Nc2nc(C)no2)cc([C@@H](C)c2ccccc2)n1] | 366.3 | 0.74 (High pH) |
| 75 | (S)-$N^2$-Methyl-$N^4$-(5-methyl-1,3,4-oxadiazol-2-yl)-6-(1-phenylethyl)pyridine-2,4-dicarboxamide | 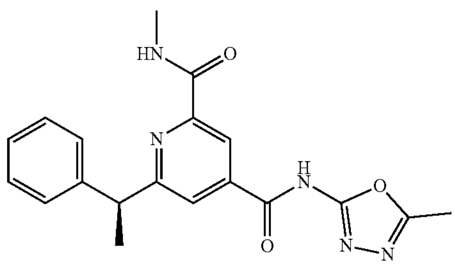 [SMILES: CNC(=O)c1cc(C(=O)Nc2nnc(C)o2)cc([C@@H](C)c2ccccc2)n1] | 366.3 | 0.74 (High pH) |
| 76 | (S)-$N^2$-Methyl-$N^4$-(4-methyl-4H-1,2,4-triazol-3-yl)-6-(1-phenylethyl)pyridine-2,4-dicarboxamide | 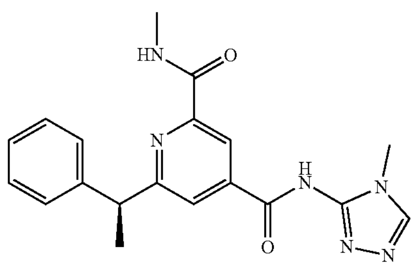 [SMILES: CNC(=O)c1cc(C(=O)Nc2nncn2C)cc([C@@H](C)c2ccccc2)n1] | 365.3 | 0.77 (High pH) |
| 81 | 6-Benzyl-$N^2$-methylpyridine-2,4-dicarboxamide | 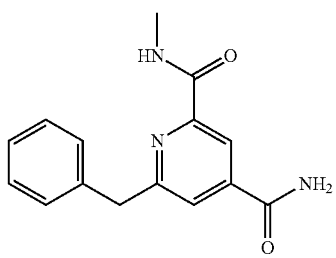 [SMILES: CNC(=O)c1cc(C(N)=O)cc(Cc2ccccc2)n1] | 270.1 | 0.78 (Formic) |

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

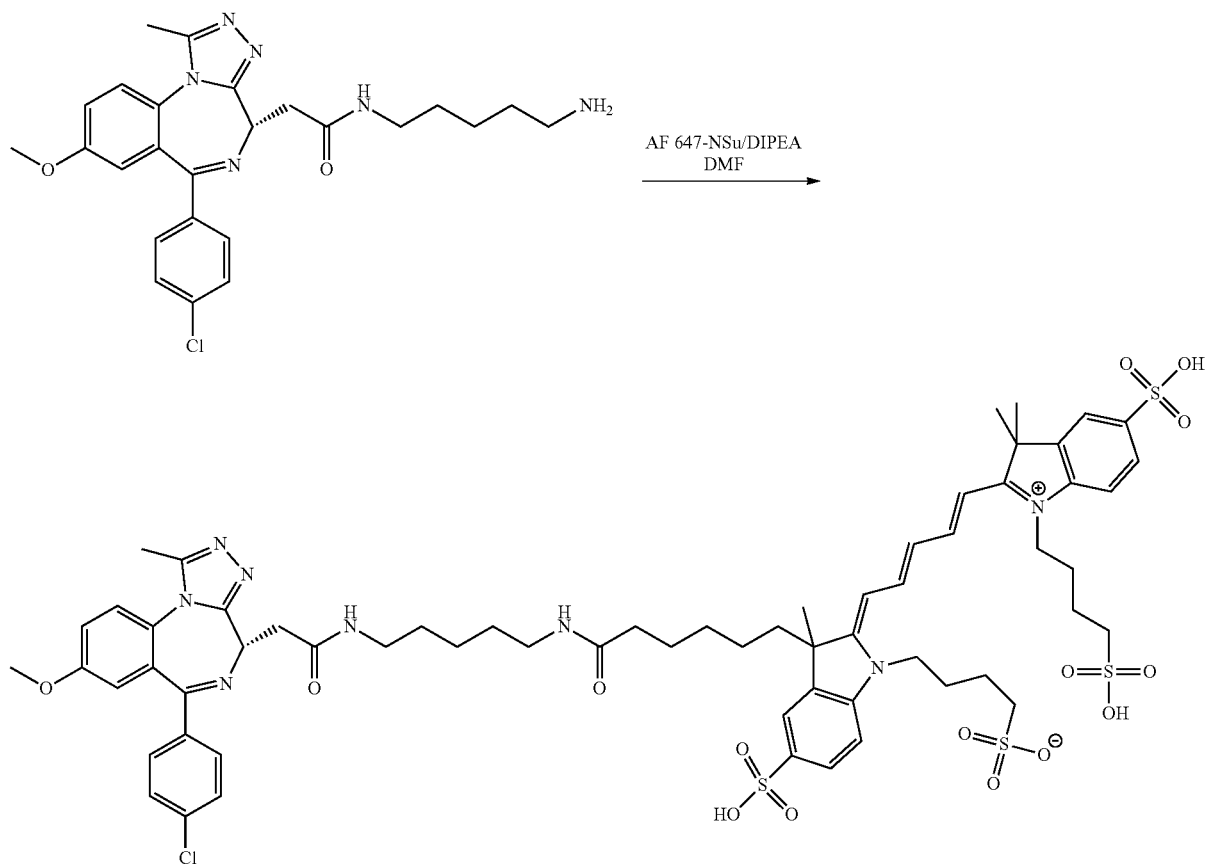

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 µmol) in DMF (40 µL) was added a solution of AlexaFluor647-ONSu (2.16 mg, 1.966 µmol) also in DMF (100 µL). The mixture was basified with DIPEA (1 µl, 5.73 µmol) and agitated overnight on a vortex mixer.

The reaction mixture was evaporated to dryness. The solid was dissolved in MeCN/water/AcOH (5/4/1, <1 mL) filtered and was applied to a Phenomenex Jupiter C18 preparative column and eluted with the following gradient (A=0.1% trifluoroacetic acid in water, B=0.1% TFA/90% MeCN/10% water): Flow rate=10 mL/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M+H]$^+$ (obs): 661.8/– corresponding with M-29. This equates to [(M+2H)/2]$^+$ for a calculated mass of 1320.984 which is M-29. This is a standard occurrence with the Alexa Fluor 647 dye and represents a theoretical loss of two methylene groups under the conditions of the mass spectrometer.

Assay Principle:

In order to generate a TR-FRET signal, donor fluorophore is excited by a laser at λ337 nm, which subsequently leads to emission at λ618 nm. If the acceptor fluorophore is in close proximity then energy transfer can occur, which leads to emission of Alexa Fluor® 647 at λ665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly reduced in comparison to the non mutated, wild type tandem BET proteins (>1000 fold reduction in Kd). The affinities of the single mutated bromdomain tandem proteins for Reference Compound X were equipotent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein Production:

Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH 7.5), 300 mM NaCl, 10 mM imidazole & 1 µL/mL protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH 7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant TR-FRET Competition Assays:

All assay components were dissolved in an assay buffer composing of 50 mM HEPES pH 7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at λ337 nm and subsequently, after a delay of 50 µsecs, measuring emission of the donor and acceptor fluorophores at λ615 nm and λ665 nm, respectively. In order to control these assays, 16 replicates each of uninhibited (DMSO vehicle) and inhibited (10*$IC_{50}$ concentrations of Example 11 of WO 2011/054846A1) TR-FRET assays were included on every microtitre plate.

cA four parameter curve fit of the following form was then applied:

$$y=a+((b-a)/(1+(10\char`\^x/10\char`\^c)\char`\^d))$$

Where 'a' is the minimum, 'b' is the Hill slope, 'c' is the $pIC_{50}$ and 'd' is the maximum.

All compounds (Examples) were each tested in the BRD4 BD1 and the BRD4 BD2 TR-FRET assays essentially as described above. Those of skill in the art will recognise that in vitro binding assays and cell-based assays for functional activity are subject to experimental variability. Accordingly, it is to be understood that the $pIC_{50}$ values given below are exemplary only. $pIC_{50}$ values are expressed as $log_{10}$ units.

All Examples, with the exemption of Example 72, were found to have a $pIC_{50} \geq 5.0$ in at least one assay described above.

Examples 59, 61, 66 and 74-76 were found to have a $pIC_{50} \geq 5.0$ and <6.0 in the BRD4 BD2 assay.

All other tested compounds were found to have a $pIC_{50} \geq 6.0$ and <8.1 in the BRD4 BD2 assay. In particular, Example 11 was found to have a $pIC_{50}$ of 7.8 (n=2) in the BRD4 BD2 assay; Example 12 was found to have a $pIC_{50}$ of 7.7 (n=8) in the BRD4 BD2 assay; Example 16 was found to have a $pIC_{50}$ of 8.0 (n=5) in the BRD4 BD2 assay; and Example 55 was found to have a $pIC_{50}$ of 7.7 (n=3) in the BRD4 BD2 assay.

Calculation of Selectivity for BRD4 BD2 Over BRD4 BD1

Selectivity for BRD4 BD2 over BRD4 BD1 was calculated as follows:

Selectivity=BRD4 BD2 $pIC_{50}$−BRD4 BD1 $pIC_{50}$

All Examples, with the exemption of Examples 62 and 72, were found to have selectivity for BRD4 BD2 over BRD4 BD1 of ≥1 log unit in at least one of the TR-FRET assays described above, and hence are at least 10 fold selective for BRD4 BD2 over BRD4 BD1.

Examples 1 to 56 and 78-80 were found to have selectivity for BRD4 BD2 over BRD4 BD1 of ≥2 log unit in at least one of the TR-FRET assays described above, and hence are at least 100 fold selective for BRD4 BD2 over BRD4 BD1.

Example 11, 12 and 55 were found to have selectivity for BRD4 BD2 over BRD4 BD1 of 2.7 log units in at least one of the TR-FRET assays described above.

Example 16 was found to have a selectivity for BRD4 BD2 over BRD4 BD1 of 3.0 log units in at least one of the TR-FRET assays described above, and hence 1000-fold selective for BRD4 BD2 over BRD4 BD1.

The invention claimed is:
1. A compound of Formula (I)

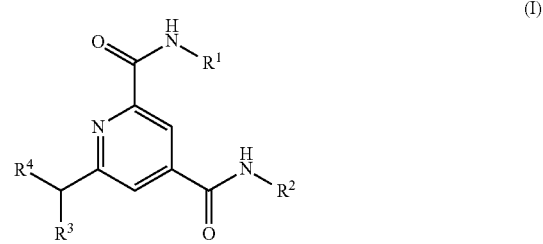

(I)

or a pharmaceutically acceptable salt thereof
wherein:
$R^1$ is —$C_{1-3}$alkyl or cyclopropyl;
$R^2$ is H, —$CH_3$, $C_{2-6}$alkyl optionally substituted by one, two, three, four, or five fluorine atoms, —$C_{2-6}$ alkyl$OR^7$, —$C_{2-6}$ alkyl$NR^7R^8$, —$(CH_2)_mSO_2C_{1-3}$alkyl, —$(CH_2)_mC(O)NR^7R^8$, —$(CH_2)_mCN$, —$(CH_2)_mCO_2R^7$, -$(CH_2)_mNHCO_2C(CH_3)_3$,
or $R^2$ is —$(CH_2)_nC_{5-6}$heteroaryl wherein $C_{5-6}$heteroaryl is optionally substituted by one or two substituents independently selected from halo, —$C_{1-4}$alkyl, —$C_{3-4}$cycloalkyl, and —$C_{0-4}$alkyl$OR^5$;
$R^3$ is H, —$C_{1-4}$alkyl, cyclopropyl, fluoro, chloro, —$CH_2F$, —$C_{0-3}$alkyl$OR^5$, or —$C_{0-3}$alkylCN;
$R^4$ is phenyl or a heteroaryl group wherein each are optionally substituted by one, two, or three $R^6$ groups which may be the same or different;
$R^5$ is H or —$C_{1-3}$alkyl;

each $R^6$ is independently halo, —$C_{1-4}$alkyl, —$C_{0-3}$alkylOR$^7$, —$C_{0-3}$alkylNR$^9$R$^{10}$, —$C_{0-3}$alkyl-CONR$^9$R$^{10}$, —CN, oxo, —SO$_2$—$C_{1-3}$alkyl, or —SO$_2$NR$^9$R$^{10}$;

$R^7$ and $R^8$ are each independently selected from —H, —$C_{1-3}$alkyl, and —$C_{2-4}$alkylOC$_{0-3}$alkyl;

$R^9$ and $R^{10}$ are each independently selected from —H and —$C_{1-3}$alkyl; or $R^9$ and $R^{10}$ may join together with the nitrogen to which they are attached, to form a 4 to 7-membered heterocyclyl optionally substituted by one or two substituents independently selected from —$C_{1-3}$alkyl optionally substituted with up to 3 fluorine atoms, —$C_{2-4}$alkylOH, —OH, and F;

m is an integer selected from 2, 3, or 4; and n is an integer selected from 0, 1, 2, 3, or 4.

2. The compound or pharmaceutically acceptable salt thereof according to claim 1 wherein $R^1$ is methyl.

3. The compound or pharmaceutically acceptable salt thereof according to claim 1, wherein $R^2$ is methyl, ethyl, propyl, iso-propyl, butyl, —CH$_2$CH$_2$CH(CH$_3$)$_2$, —CH$_2$CH(CH$_3$)$_2$, —CH$_2$CH$_2$OR$^7$, —CH$_2$CH$_2$CH$_2$OR$^7$, —CH$_2$CH(CH$_3$)OR$^7$, —CH$_2$CH$_2$CH(CH$_3$)OR$^7$, CH$_2$CH$_2$CH(OR$^7$)$_2$, —CH$_2$CH$_2$CH(CH$_3$)NR$^7$R$^8$, —CH$_2$CH$_2$CH$_2$NR$^7$R$^8$, —(CH$_2$)$_m$SO$_2$CH$_3$, —(CH$_2$)$_m$C(O)NHCH$_3$, —(CH$_2$)$_m$CN, —(CH$_2$)$_m$CO$_2$R$^7$, —(CH$_2$)$_m$CF$_3$, and —(CH$_2$)$_m$NHCO$_2$C(CH$_3$)$_3$.

4. The compound or pharmaceutically acceptable salt thereof according to claim 1, wherein $R^2$ is —(CH$_2$)$_n$C$_{5-6}$heteroaryl wherein the C$_{5-6}$heteroaryl is selected from furanyl, thienyl, pyrrolyl, triazolyl, thiazolyl, oxazolyl, isoxazolyl, oxadiazolyl, imidazolyl, pyrazolyl, triazolyl, tetrazolyl, isoxazolyl, pyridinyl, pyridazinyl, pyrazinyl, and pyrimidinyl, wherein said furanyl, thienyl, pyrrolyl, triazolyl, thiazolyl, oxazolyl, isoxazolyl, oxadiazolyl, imidazolyl, pyrazolyl, triazolyl, tetrazolyl, isoxazolyl, pyridinyl, pyridazinyl, pyrazinyl, or pyrimidinyl is optionally substituted by one or two substituents independently selected from halo, C$_{1-4}$alkyl, C$_{3-4}$cycloalkyl, and —C$_{0-3}$alkylOR$^5$.

5. The compound or pharmaceutically acceptable salt thereof according to claim 4, wherein the C$_{5-6}$ heteroaryl is pyrazolyl optionally substituted by C$_{1-4}$alkyl or —C$_{0-3}$alkylOR$^5$.

6. The compound or pharmaceutically acceptable salt thereof according to claim 1, wherein $R^3$ is —H, methyl, fluoro, —OCH$_3$, or —OH.

7. The compound or pharmaceutically acceptable salt thereof according to claim 1, wherein $R^4$ is phenyl optionally substituted by one, two, or three $R^6$ groups which may be the same or different.

8. The compound or pharmaceutically acceptable salt thereof according to claim 1, wherein $R^4$ is a heteroaryl group which is indolyl optionally substituted by one, two, or three $R^6$ groups which may be the same or different.

9. The compound or pharmaceutically acceptable salt thereof according to claim 8, wherein $R^4$ is 1H-indol-4-yl.

10. The compound or pharmaceutically acceptable salt thereof according to claim 1, wherein n is 0 or 2.

11. The compound or pharmaceutically acceptable salt thereof according to claim 1, wherein m is 2.

12. A compound which is selected from
6-Benzyl-N$^2$-methyl-N$^4$-(1-methyl-1H-pyrazol-4-yl)pyridine-2,4-dicarboxamide;
6-Benzyl-N$^2$-methyl-N$^4$-(1H-pyrazol-4-yl)pyridine-2,4-dicarboxamide;
(S)-N$^2$-Methyl-6-(1-phenylethyl)-N$^4$-(1H-pyrazol-4-yl)pyridine-2,4-dicarboxamide; and
(S)-6-(Methoxy(phenyl)methyl)-N$^2$-methyl-N$^4$-(1H-pyrazol-4-yl)pyridine-2,4-dicarboxamide;
or a pharmaceutically acceptable salt thereof.

13. A pharmaceutical composition comprising a compound or a pharmaceutically acceptable salt thereof according to claim 1 and one or more pharmaceutically acceptable excipients.

14. A combination comprising a compound or a pharmaceutically acceptable salt thereof according to claim 1 together with one or more other therapeutically active agents.

15. A method of non-prophylactic treatment of a disease or condition in a human for which a bromodomain inhibitor is indicated, the method comprising administering to the human in need thereof a therapeutically effective amount of the compound or pharmaceutically acceptable salt thereof as according to claim 1.

16. The method of treatment according to claim 15, wherein the disease or condition is an acute or chronic autoimmune and/or inflammatory condition.

17. The method of treatment according to claim 15, wherein the disease or condition involves an inflammatory response to an infection with bacteria, a virus, fungi, a parasite, or their toxins.

18. The method of treatment according to claim 15, wherein the disease or condition is a viral infection.

19. The method of treatment according to claim 14, wherein the disease or condition is cancer.

20. The method of treatment according to claim 15, wherein the disease or condition is rheumatoid arthritis.

* * * * *